(12) United States Patent
Telerman et al.

(10) Patent No.: US 6,503,502 B1
(45) Date of Patent: Jan. 7, 2003

(54) NUCLEOTIDE SEQUENCES, PROTEINS, DRUGS AND DIAGNOSTIC AGENTS OF USE IN TREATING CANCER

(75) Inventors: Adam Telerman; Robert Amson; Daniel Cohen, all of Paris (FR)

(73) Assignee: Société Molecular Engines Laboratories a French Société anonyme, Paris (FR)

( * ) Notice: Subject to any disclaimer, the term of this patent is extended or adjusted under 35 U.S.C. 154(b) by 0 days.

(21) Appl. No.: 09/544,618

(22) Filed: Apr. 6, 2000

Related U.S. Application Data

(60) Division of application No. 09/134,873, filed on Aug. 17, 1998, now abandoned, which is a continuation-in-part of application No. 09/091,647, filed as application No. PCT/FR96/02061 on Dec. 20, 1996, now abandoned.

(30) Foreign Application Priority Data

Dec. 20, 1995 (FR) ............................................. 95 15146
Apr. 18, 1996 (FR) ............................................. 96 04854

(51) Int. Cl.$^7$ .......................... A01N 63/00; C07H 21/04; C12N 15/00; C12N 15/63; C12N 5/00
(52) U.S. Cl. .................... 424/93.2; 536/23.1; 536/23.5; 435/320.1; 435/325; 435/455
(58) Field of Search .............................. 536/23.1, 23.5; 435/320.1, 325, 455; 514/44; 424/93.2

(56) References Cited

FOREIGN PATENT DOCUMENTS

| WO | 95/11301 | 4/1995 |
| WO | 95/19367 | 7/1995 |

OTHER PUBLICATIONS

Amson et al., GenEmbl Accession No. U50962, p. 2. Aug. 1996.
Sherrington et al., GenEmbl Accession No. L42177, p. 3, 4. Jul. 1995.
Miller et al., Targeted vector for gene therapy, Feb. 1995, FASEB, vol. 9, pp. 190–199.*
Verma et al., Gene therapy promises, problems and propects, Sep. 1997, Nature, vol. 389, pp. 239–242.*
Crystal et al., Transfer of Genes to Humans: Early Lessons and Obstacles to Success, 1995, Science, vol. 270, pp. 404–410.*
Deonarain, Ligand–targeted receptor–mediated vectors for gene delivery, 1998, Ashley Publication Ltd., p. 53–69.*
Eck et al., Gene–Based Therapy, 1996, Goodman & Gilan's The Pharmacological Basis of Therapeutics, Ninth Edition, pp. 77–101.*

L42177, Gen Bank, Jul. 24, 1995.*
Lee et al., "Purification, Molecular cloning, and Sequencing of Phospholipase C–B4*", J. Biol. Chem., vol. 268, No. 28, (1993), pp 21318–21327.
Toda et al., Isolation, and Characterization of a Novel Gene Encoding Nuclear Protein at locus (D11S636). Human Molecular Genetics, vol. 3, No. 3, (1994), pp 465–470.
Della et al., Isolation and characterization of Murine Homolgues of the Drosophila Seven in Absential Gene. Development, vol. 117, No. 4, (1993), pp 1333–1343.
Guenal, Studies of Specific Gene Induction During apoptosis of Cell Lines Conditionally Immortalized by FEBS Lett, vol. 374, No. 3 (1995), pp 384–386.
Zhan et al., Induction of bax by Genotoxic Stress in Human Cells Correlates With Normal P53 Status and. Oncogene, vol. 9, No. 12, (1994), pp 3743–03751.
Liang et al., "Differential Display of Eukaryotic Messenger RNA by Means of the Polymerase Chain Reaction", Science, vol. 257, (1992), pp 967–971.
Don et al., "Touchdown PCR to Circumvent Spurious Priming During Gene Amplification", Nucleic Acids Research, vol. 19, No. 14, (1991).
Hillier et al., "Voir L'Alignements des Sequences Nucleotidiques et Proteiques; Les Descripteurs", Unpublished (1995).
Hillier et al., "Voir L'Alignements des Sequences Nucleotidiques et Proteiques; Les Descripteurs", Unpublished (1996).
Amson et al., Isolation of 10 Differentially Expressed cDNAs in p53–induced Apoptosis: Activation of the Proc Natl. Acad. Sci., vol. 93, No. 9, (1996), pp 3952–3957.
Nemani et al., Activation of the Human Homologue of the Drosphila Sina Gene in Apoptosis and tumor Proc. Nat'l Acad. Sci., vol. 93, No. 17, (1996), pp 9039–9042.
Sherrington et al., "Cloning of a Gene Bearing Missense Mutations in Early–Onset Familial Aizheimer's. Disease", Nature, vol. 375, (1995), pp 754–760.
Della et al., "A Combined Genetic and Biochemical Approach to Mammalian Signal Transduction", Australian and New Zealand Journal of Medicine, vol. 25, No. 6, (1995), pp 845–851.

* cited by examiner

Primary Examiner—Deborah J. R. Clark
Assistant Examiner—Shin-Lin Chen
(74) Attorney, Agent, or Firm—Foley & Lardner

(57) ABSTRACT

Tumor Suppressor Activated Pathway (TSAP) genes and nucleotide sequences therefore as well as vectors and cells containing such nucleotide sequences and various uses therefore are described. The mechanism by which TSAP 3 activates apoptosis also is described. Pharmaceutical compositions and methods for preventing tumorigenesis also is described.

9 Claims, 18 Drawing Sheets

FIG. 4

```
TSAP1
          10                                         TGATCACGTAC
                                                     : ::::
ratPLC    CTTCTTCTACTTAACAATTTGACTATTGAATTTCTTTGGCCAACCAAAAGTAGCTATGTAC
          3970      3980      3990      4000      4010      4020

20        30        40        50        60        70
TSAP 1    ACACACACACACAGAGAGAGAGAGAGAGAGAGAGAGGGGGAGAGAGAGAGAGAGAGAT
          ::::::::::::: : : : : :                  : : : : : ::: ::
ratPLC    ACACACACACACACACACACACACACACA-----------CACACACACACACACAGAAAT
          4030      4040                4050      4060

80        90        100       110       120       130
TSAP 1    CCCCTATTCCTGACAGGCAGAGTTGAATCATGATATATGGCTTAAACATGTTTGCTATGA
          ::::::::::::::::::::::::::::: ::: ::  :  ::::::::::::: :::: :
ratPLC    CCCCTATTCCTGACAGGCAGAGTTGAACCATAATCCACAACTTAAACATGTTGGCTAGGG
          4070      4080      4090      4100      4110      4120

140       150       160       170       180       190
TSAP 1    GACAGCATCACAAGCCAGTGGGCTTGGTGATAACAACTCTGCTTTGTGGTGCATTAGGAC
          ::::::::::::::::::::::::::::::::::::::::::::::::::::::::::::
ratPLC    GACAGCATCACAAGCCAGTGGGCTTGGTGATAACAACTCTGCTTTGTGGTGCATTAGGAC
          4130      4140      4150      4160      4170      4180

200       210       220       230
TSAP 1    ATTTTTGAGCTGCTGCTGCTGCAAA-AAAAATAAGAGCCG
          :: ::  ::::::::::::   :::  ::::: :: ::
ratPLC    ATGTTCGAGCTGCTGCTG--GAAAAGGAAAATTAGTGCATTAGTACTTTAATGGCAAGCG
          4190      4200      4210      4220      4230      4240
```

FIG. 5

```
TSAP2
        10        20        30        40        50        60
TSAP2         GCTTGGAACCAATCTACAACAGCGAGGGGAAGCGGCTTAACACTCGAGAGTTCCGTACCC
              :: ::  :::::::::  ::::::::::::::::::::::  :::::::::::  ::::
humzfmlc.seq  CCCCTGAGCCCATCTACAATAGCGAGGGGAAGCGGCTTAACACCCGAGAGTTCCGCACCC
              250       260       270       280       290       300

70        80        90        100       110       120
TSAP2         GCAAAAAAAAAAAATCTCTTGTGTTTTCCTAAGCTTTTCCCTGTGCTAGGGAAAGATCAGT
              ::::::::
humzfmlc.seq  GCAAAAAGCTGGAAGAGGAGCGGCACAACCTCATCACAGAGATGGTTGCACTCAATCCGG
              310       320       330       340       350       360

130       140
TSAP2         AAGTCCGTGGTTATAGATTGGTT humzfmlc.seq  ATTTCAAGCCACCTGCAGATTACAAACCTCCAGCAACACGTGTGAGTGAT
              370       380       390       400       410
```

FIG. 6

```
TSAP3
10
TSAP3 3                                                          TTTTTTTTTTTG
                                                                 : : : :
mmsiah1b.seq TTGTAAAATATTTCTGAACTTTGTATTTGTTGTAGATTGATTGTATTGTTGACAATTTTT
             1450      1460      1470      1480      1490      1500

20        30        40        50        60        70
TSAP 3       CGGGGTGGGGGTGTGCCTGCACACATGCGTGCACGTGTGTGCTTGGTTTTCCTTTAACAA
             ::::::::::::::::::::::::::::::::::::::::::::::::::::::::::::
mmsiah1b.seq CGGGGTGGGGGTGTGCCTGCACACATGCGTGCACGTGTGTGCTTGGTTTTCCTTTAACAA
             1510      1520      1530      1540      1550      1560

80        90        100       110       120       130
TSAP 3       GCCATCTACGTGTCATAGCCCACTGTTTTCCCCTTGTGAGTCAACACATAGTGCTGCTGT
             ::::::::::::::::::::::::::::::::::::::::::::::::::::::::::::
mmsiah1b.seq GCCATCTACGTGTCATAGCCCACTGTTTTCCCCTTGTGAGTCAACACATAGTGCTGCTGT
             1570      1580      1590      1600      1610      1620

140
TSAP3        GGTTTGGGTTTGGT
             :::::  ::::::::::
mmsiah1b.seq GGTTTTGGTTTGGTTTGCTTTTGGTTTTTGATGTGTGTGTATTTGATAATTTTTATTCTA
             1630      1640      1650      1660      1670      1680
```

FIG. 7

```
HUMSIAH      ---------------MSRQTATALPTGTSKCPPSQRVPALTGTTASNN------------
MMSIAH1A_1   ---------------MSRQTATALPTGTSKCPPSQRVPALTGTTASNN------------
MMSIAH1B_1   ---------------MSRQAATALSTGTSKCPPSQRVPALTDTTASNN------------
DROSINA_I    MSNKINPKRREPTAAAAGAGATGVATNTSTSTGSSSAGNTSSANTSSSSSSSSLSSAGGGD
                            **  * **    *                *   .   *

HUMSIAH      -----DLASLFECPVCFDYVLPPILQCQSGHLVCSNCRPKLTCCPTCRGPLGSIRNLAME
MMSIAH1A_1   -----DLASLFECPVCFDYVLPPILQCQSGHLVCSNCRPKLTCCPTCRGPLGSIRNLAME
MMSIAH1B_1   -----DLASLFECPVCFDYVLPPILQCQSGHLVCSNCRPKLTCCPTCRGPLGSIRNLAME
DROSINA_I    AGMSADLTSLFECPVCFDYVLPPILQCSSGHLVCVSCRSKLTCCPTCRGPLANIRNLAME
                 ** .******************* ****** ** *********** ******

HUMSIAH      KVANSVLFPCKYASSGCEITLPHTEKADHEELCEFRPYSCPCPGASCKWQGSLDAVMPHL
MMSIAH1A_1   KVANSVLFPCKYASSGCEITLPHTEKAEHEELCEFRPYSCPCPGASCKWQGSLDAVMPHL
MMSIAH1B_1   KVANSVLFPCKYSASGCEITLPHTKKAEHEELCEFRPYSCPCPGASCKWQGSLDAVMPHL
DROSINA_I    KVASNVKFPCKHSGYGCTASLVYTEKTEHEETCECRPYLCPCPGASCKWQGPLDLVMQHL
             ***  * ****  .   **   .    * *  *** *** *** *********   .

HUMSIAH      MHQHKSITTLQGEDIVFLATDINLPGAVDWVMMQSCFGFHFMLVLEKQEKYDGHQQFFAI
MMSIAH1A_1   MHQHKSITTLQGEDIVFLATDINLPGAVDWVMMQSCFGFHFMLVLEKQEKYDGHQQFFAI
MMSIAH1B_1   MHQHKSITTLQGEDIVFLATDINLPGAVDWVMMQSCFGFHFMLVLEKQEKYDGHQQFFAT
DROSINA_I    MMSHKSITTLQGEDIVFLATDINLPGAVDWVMMQSCFGHHFMLVLEKQEKYDGHQQFFAI
             *  ************************************ *******************

HUMSIAH      VQLIGTRKQAENFAYRLELNGHRRRLTWEATPRSIHEGIATAIMNSDCLVFEPSIAQLFA
MMSIAH1A_1   VQLIGTRKQAENFAYRLELNGHRRRLTWEATPRSIHEGIATAIMNSDCLVFDTSIAQLFA
MMSIAH1B_1   VQLIGTRKQAENFAYRLELNGHRRRLTWEATPRSIHEGIATAIMNSDCLVFDTSIAQLFA
DROSINA_I    VQLIGSRKEAENFVYRLELNGNRRRLTWEAMPRSIHEGVASAIHNSDCLVFDTSIAQLFA
             ***** **.**** ******* ******** ******  . **  ******  ******

HUMSIAH      ENGNLGINVTISMC
MMSIAH1A_1   ENGNLGINVTISMC
MMSIAH1B_1   ENGNLGINVTISMC
DROSINA_I    DNGNLGINVTISLV
             .**********.
```

FIG. 8A

|  |  | 10 | 20 | 30 |
|---|---|---|---|---|
| 1 mms182 | | ---------- | ---------- | ---------- |
| 3 | | ********** | ********** | ********** |
| 2 tsip2 | | CACCGGTGAG | ACCTCTAGGG | CGGGGCCTAG |
|  |  | 40 | 50 | 60 |
| 1 mms182 | | ---------- | ---------- | ---------- |
| 3 | | ********** | ********** | ********** |
| 2 tsip2 | | GACGACCTGC | TCCGTGGGCC | GCGAGTATTC |
|  |  | 70 | 80 | 90 |
| 1 mms182 | | -------acc | anacancggc | agctgaggcg |
| 3 | | ******--* | -*----*---- | ---------- |
| 2 tsip2 | | GTCGGAAACA | AAACAGCGGC | AGCTGAGGCG |
|  |  | 100 | 110 | 120 |
| 1 mms182 | | gaaacctagg | ctgcgagccg | gccgcccggg |
| 3 | | ---------- | ---------- | ---------- |
| 2 tsip2 | | GAAACCTAGG | CTGCGAGCCG | GCCGCCCGGG |
|  |  | 130 | 140 | 150 |
| 1 mms182 | | cgcggagaga | gaaggaacca | acacaagaca |
| 3 | | ---------- | ---------- | ---------- |
| 2 tsip2 | | CGCGGAGAGA | GAAGGAACCA | ACACAAGACA |
|  |  | 160 | 170 | 180 |
| 1 mms182 | | cgagcccttc | gaggtcttta | ggcagcttgg |
| 3 | | ---------- | ---------- | ---------- |
| 2 tsip2 | | GCAGCCCTTC | GAGGTCTTTA | GGCAGCTTGC |
|  |  | 190 | 200 | 210 |
| 1 mms182 | | aggagaacac | atgagagaaa | gaatcccaag |
| 3 | | ---------- | ---------- | ---------- |
| 2 tsip2 | | AGGAGAACAC | ATGAGAGAAA | GAATCCCAAG |
|  |  | 220 | 230 | 240 |
| 1 mms182 | | aggttttgtt | ttctttgaga | aggtatttct |
| 3 | | ---------- | ---------- | ---------- |
| 2 tsip2 | | AGGTTTTGTT | TTCTTTGAGA | AGGTATTTCT |
|  |  | 250 | 260 | 270 |
| 1 mms182 | | gtccagctgc | tccaatgaca | gagatacctg |
| 3 | | ---------- | ---------- | ---------- |
| 2 tsip2 | | GTCCAGCTGC | TCCAATGACA | GAGATACCTG |
|  |  | 280 | 290 | 300 |
| 1 mms182 | | cacctttgtc | ctacttccag | aatgcccaga |
| 3 | | ---------- | ---------- | ---------- |
| 2 tsip2 | | CACCTTTGTC | CTACTTCCAG | AATGCCCAGA |
|  |  | 310 | 320 | 330 |
| 1 mms182 | | tgtctgagga | cagccactcc | agcagcgcca |
| 3 | | ---------- | ---------- | ---------- |
| 2 tsip2 | | TGTCTGAGGA | CAGCCACTCC | AGCAGCGCCA |

FIG. 8B

| | 340 350 360 |
|---|---|
| 1 mms182 | tccggagcca gaatgacagc caagaacggc |
| 3 | ---------- ---------- ---------- |
| 2 tsip2 | TCCGGAGCCA GAATGACAGC CAAGAACGGC |
| | 370 380 390 |
| 1 mms182 | agcagcagca tgacaggcag agacttgaca |
| 3 | ---------- ---------- ---------- |
| 2 tsip2 | AGCAGCAGCA TGACAGGCAG AGACTTGACA |
| | 400 410 420 |
| 1 mms182 | accctgagcc aatatctaat gggcggcccc |
| 3 | ---------- ---------- ---------- |
| 2 tsip2 | ACCCTGAGCC AATATCTAAT GGGCGGCCCC |
| | 430 440 450 |
| 1 mms182 | agagtaactc aagacaggtg gtggaacaag |
| 3 | ---------- ---------- ---------- |
| 2 tsip2 | AGAGTAACTC AAGACAGGTG GTGGAACAAG |
| | 460 470 480 |
| 1 mms182 | atgaggagga agacgaagag ctgacattga |
| 3 | ---------- ---------- ---------- |
| 2 tsip2 | ATGAGGAGGA AGACGAAGAG CTGACATTGA |
| | 490 500 510 |
| 1 mms182 | aatatggagc caagcatgtc atcatgctct |
| 3 | ---------- ---------- ---------- |
| 2 tsip2 | AATATGGAGC CAAGCATGTC ATCATGCTCT |
| | 520 530 540 |
| 1 mms182 | ttgtccccgt gaccctctgc atggtcgtcg |
| 3 | ---------- ---------- ---------- |
| 2 tsip2 | TTGTCCCCGT GACCCTCTGC ATGGTCGTCG |
| | 550 560 570 |
| 1 mms182 | tcgtggccac catcaaatca gtcagcttct |
| 3 | ---------- ---------- ---------- |
| 2 tsip2 | TCGTGGCCAC CATCAAATCA GTCAGCTTCT |
| | 580 590 600 |
| 1 mms182 | atacccggaa ggacggtcag ctaatctaca |
| 3 | ---------- ---------- ---------- |
| 2 tsip2 | ATACCCGGAA GGACGGTCAG CTAATCTACA |
| | 610 620 630 |
| 1 mms182 | ccccattcac agaagacact gagactgtag |
| 3 | ---------- ---------- ---------- |
| 2 tsip2 | CCCCATTCAC AGAAGACACT GAGACTGTAG |
| | 640 650 660 |
| 1 mms182 | gccaaagagc cctgcactcg atcctgaatg |
| 3 | ---------- ---------- ---------- |
| 2 tsip2 | GCCAAAGAGC CCTGCACTCG ATCCTGAATG |

FIG. 8C

|   |   |   |   |
|---|---|---|---|
|   |   | 670 680 | 690 |
| 1 mms182 | | cggccatcat gatcagtgtc | attgtcatta |
| 3 2 tsip2 | | CGGCCATCAT GATCAGTGTC | ATTGTCATTA |
|   |   | 700 710 | 720 |
| 1 mms182 | | tgaccatcct cctggtggtc | ctgtataaat |
| 3 2 tsip2 | | TGACCATCCT CCTGGTGGTC | CTGTATAAAT |
|   |   | 730 740 | 750 |
| 1 mms182 | | acaggtgcta caaggtcatc | cacgcctggc |
| 3 2 tsip2 | | ACAGGTGCTA CAAGGTCATC | CACGCCTGGC |
|   |   | 760 770 | 780 |
| 1 mms182 | | ttattatttc atctctgttg | ttgctgttct |
| 3 2 tsip2 | | TTATTATTTC ATCTCTGTTG | TTGCTGTTCT |
|   |   | 790 800 | 810 |
| 1 mms182 | | tttttcgtt catttactta | ggggaagtat |
| 3 2 tsip2 | | TTTTTTCGTT CATTTACTTA | GGGGAAGTAT |
|   |   | 820 830 | 840 |
| 1 mms182 | | ttaagaccta caatgtcgcc | gtggactacg |
| 3 2 tsip2 | | TTAAGACCTA CAATGTCGCC | GTGGACTACG |
|   |   | 850 860 | 870 |
| 1 mms182 | | ttacagtagc actcctaatc | tggaattttg |
| 3 2 tsip2 | | TTACAGTAGC ACTCCTAATC | TGGAATTTTG |
|   |   | 880 890 | 900 |
| 1 mms182 | | gtgtggtcgg gatgattgcc | atccactgga |
| 3 2 tsip2 | | GTGTGGTCGG GATGATTGCC | ATCCACTGGA |
|   |   | 910 920 | 930 |
| 1 mms182 | | aaggcccct tcgactgcag | caggcgtatc |
| 3 2 tsip2 | | AAGGCCCCCT TCGACTGCAG | CAGGCGTATC |
|   |   | 940 950 | 960 |
| 1 mms182 | | tcattatgat cagtgccctc | atggccctgg |
| 3 2 tsip2 | | TCATTATGAT CAGTGCCCTC | ATGGCCCTGG |
|   |   | 970 980 | 990 |
| 1 mms182 | | tatttatcaa gtacctcccc | gaatggaccg |
| 3 2 tsip2 | | TATTTATCAA GTACCTCCCC | GAATGGACCG |

FIG. 8D

| | | | | |
|---|---|---|---|---|
| | | 1000 | 1010 | 1020 |
| 1 mms182 | | catggctcat | cttggctgtg | atttcagtat |
| 3 | | --------- | ---------- | ---------- |
| 2 tsip2 | | CATGGCTCAT | CTTGGCTGTG | ATTTCAGTAT |
| | | 1030 | 1040 | 1050 |
| 1 mms182 | | atgatttggt | ggctgtttta | tgtcccaaag |
| 3 | | ---------- | ---------- | ---------- |
| 2 tsip2 | | ATGATTTGGT | GGCTGTTTTA | TGTCCCAAAG |
| | | 1060 | 1070 | 1080 |
| 1 mms182 | | gcccacttcg | tatgctggtt | gaaacagctc |
| 3 | | ---------- | ---------- | ---------- |
| 2 tsip2 | | GCCCACTTCG | TATGCTGGTT | GAAACAGCTC |
| | | 1090 | 1100 | 1110 |
| 1 mms182 | | aggaaagaaa | tgagactctc | tttccagctc |
| 3 | | ---------- | ---------- | ---------- |
| 2 tsip2 | | AGGAAAGAAA | TGAGACTCTC | TTTCCAGCTC |
| | | 1120 | 1130 | 1140 |
| 1 mms182 | | ttatctattc | ctcaacaatg | gtgtggttgg |
| 3 | | ---------- | ---------- | ---------- |
| 2 tsip2 | | TTATCTATTC | CTCAACAATG | GTGTGGTTGG |
| | | 1150 | 1160 | 1170 |
| 1 mms182 | | tgaatatggc | tgaaggagac | ccagaagccc |
| 3 | | ---------- | ---------- | ---------- |
| 2 tsip2 | | TGAATATGGC | TGAAGGAGAC | CCAGAAGCCC |
| | | 1180 | 1190 | 1200 |
| 1 mms182 | | aaaggagggt | acccaagaac | cccaagtata |
| 3 | | ---------- | ---------- | ---------- |
| 2 tsip2 | | AAAGGAGGGT | ACCCAAGAAC | CCCAAGTATA |
| | | 1210 | 1220 | 1230 |
| 1 mms182 | | acacacaaag | agcggagaga | gagacacagg |
| 3 | | ---------- | ---------- | ---------- |
| 2 tsip2 | | ACACACAAAG | AGCGGAGAGA | GAGACACAGG |
| | | 1240 | 1250 | 1260 |
| 1 mms182 | | acagtggttc | tgggaacgat | gatggtggct |
| 3 | | ---------- | ---------- | ---------- |
| 2 tsip2 | | ACAGTGGTTC | TGGGAACGAT | GATGGTGGCT |
| | | 1270 | 1280 | 1290 |
| 1 mms182 | | tcagtgagga | gtgggaggcc | caaagagaca |
| 3 | | ---------- | ---------- | ---------- |
| 2 tsip2 | | TCAGTGAGGA | GTGGGAGGCC | CAAAGAGACA |
| | | 1300 | 1310 | 1320 |
| 1 mms182 | | gtcacctggg | gcctcatcgc | tccactcccg |
| 3 | | ---------- | ---------- | ---------- |
| 2 tsip2 | | GTCACCTGGG | GCCTCATCGC | TCCACTCCCG |

FIG. 8E

| | 1330 1340 1350 |
|---|---|
| 1 mms182<br>3<br>2 tsip2 | agtcaagagc tgctgtccag gaactttctg<br>---------- ---------- ----------<br>AGTCAAGAGC TGCTGTCCAG GAACTTTCTG<br>1360 1370 1380 |
| 1 mms182<br>3<br>2 tsip2 | ggagcattct aacgagtgaa gacccggagg<br>---------- ---------- ----------<br>GGAGCATTCT AACGAGTGAA GACCCGGAGG<br>1390 1400 1410 |
| 1 mms182<br>3<br>2 tsip2 | aaagaggagt aaaacttgga ctgggagatt<br>---------- ---------- ----------<br>AAAGAGGAGT AAAACTTGGA CTGGGAGATT<br>1420 1430 1440 |
| 1 mms182<br>3<br>2 tsip2 | tcattttcta cagtgttctg gttggtaagg<br>---------- ---------- ----------<br>TCATTTTCTA CAGTGTTCTG GTTGGTAAGG<br>1450 1460 1470 |
| 1 mms182<br>3<br>2 tsip2 | cctcagcaac cgccagtgga gactggaaca<br>---------- ---------- ----------<br>CCTCAGCAAC CGCCAGTGGA GACTGGAACA<br>1480 1490 1500 |
| 1 mms182<br>3<br>2 tsip2 | caaccatagc ctgctttgta gccatactga<br>---------- ---------- ----------<br>CAACCATAGC CTGCTTTGTA GCCATACTGA<br>1510 1520 1530 |
| 1 mms182<br>3<br>2 tsip2 | tcggcctgtg ccttacatta ctcctgctcg<br>---------- ---------- ----------<br>TCGGCCTGTG CCTTACATTA CTCCTGCTCG<br>1540 1550 1560 |
| 1 mms182<br>3<br>2 tsip2 | ccattttcaa gaaagcgttg ccagccctcc<br>---------- ---------- ----------<br>CCATTTTCAA GAAAGCGTTG CCAGCCCTCC<br>1570 1580 1590 |
| 1 mms182<br>3<br>2 tsip2 | ccatctccat caccttcggg ctcgtgttct<br>---------- ---------- ----------<br>CCATCTCCAT CACCTTCGGG CTCGTGTTCT<br>1600 1610 1620 |
| 1 mms182<br>3<br>2 tsip2 | acttcgccac ggattacctt gtgcagccct<br>---------- ---------- ----------<br>ACTTCGCCAC GGATTACCTT GTGCAGCCCT<br>1630 1640 1650 |
| 1 mms182<br>3<br>2 tsip2 | tcatggacca acttgcattc catcagtttt<br>---------- ---------- ----------<br>TCATGGACCA ACTTGCATTC CATCAGTTTT |

FIG. 8F

| | |
|---|---|
| |        1660          1670          1680 |
| 1 mms182<br>3<br>2 tsip2 | atatctagcc   tttctgcagt   tagaacatgg<br>----------   ----------   ----------<br>ATATCTAGCC   TTTCTGCAGT   TAGAACATGG<br>     1690          1700          1710 |
| 1 mms182<br>3<br>2 tsip2 | atgtttcttc   tttgattatc   aaaaacacaa<br>----------   ----------   ----------<br>ATGTTTCTTC   TTTGATTATC   AAAAACACAA<br>     1720          1730          1740 |
| 1 mms182<br>3<br>2 tsip2 | aaacagagag   caagcccgag   gaggagactg<br>----------   ----------   ----------<br>AAACAGAGAG   CAAGCCCGAG   GAGGAGACTG<br>     1750          1760          1770 |
| 1 mms182<br>3<br>2 tsip2 | gtgactttcc   tgtgtcctca   gctaacaaag<br>----------   ----------   ----------<br>GTGACTTTCC   TGTGTCCTCA   GCTAACAAAG<br>     1780          1790          1800 |
| 1 mms182<br>3<br>2 tsip2 | gcaggactcc   agctggactt   ctgcagcttc<br>----------   ----------   ----------<br>GCAGGACTCC   AGCTGGACTT   CTGCAGCTTC<br>     1810          1820          1830 |
| 1 mms182<br>3<br>2 tsip2 | cttccgagtc   tccctagcca   cccgcactac<br>----------   ----------   ----------<br>CTTCCGAGTC   TCCCTAGCCA   CCCGCACTAC<br>     1840          1850          1860 |
| 1 mms182<br>3<br>2 tsip2 | tggactgtgg   aaggaagcgt   ctacagagga<br>----------   ----------   ----------<br>TGGACTGTGG   AAGGAAGCGT   CTACAGAGGA<br>     1870          1880          1890 |
| 1 mms182<br>3<br>2 tsip2 | acggtttcca   acatccatcg   ctgcagcaga<br>----------   ----------   ----------<br>ACGGTTTCCA   ACATCCATCG   CTGCAGCAGA<br>     1900          1910          1920 |
| 1 mms182<br>3<br>2 tsip2 | cggtgtccct   cagtgacttg   agagacaagg<br>----------   ----------   ----------<br>CGGTGTCCCT   CAGTGACTTG   AGAGACAAGG<br>     1930          1940          1950 |
| 1 mms182<br>3<br>2 tsip2 | acaaggaaat   gtgctgggcc   aaggagctgc<br>----------   ----------   ----------<br>ACAAGGAAAT   GTGCTGGGCC   AAGGAGCTGC<br>     1960          1970          1980 |
| 1 mms182<br>3<br>2 tsip2 | cgtgctctgc   tagctttgac   cgtgggcatg<br>----------   ----------   ----------<br>CGTGCTCTGC   TAGCTTTGAC   CGTGGGCATG |

FIG. 8G

| | | | |
|---|---|---|---|
| | 1990 | 2000 | 2010 |
| 1 mms182 | gagatttacc | cgcactgtga | actctctaag |
| 2 tsip2 | GAGATTTACC | CGCACTGTGA | ACTCTCTAAG |
| | 2020 | 2030 | 2040 |
| 1 mms182 | gtaaacaaag | tgaggtgaac | c |
| 2 tsip2 | GTAAACAAAG | TGAGGTGAAC | CAAACAGAGC |
| | 2050 | 2060 | 2070 |
| 1 mms182 | <== | | |
| 2 tsip2 | TGCCATYCTT | CCACACCATG | TTGGAAATAA |
| | 2080 | 2090 | 2100 |
| 1 mms182 | <== | | |
| 2 tsip2 | AACCGTCCTA | GCTGGAACCC | TTACTGTCCC |
| | 2110 | 2120 | 2130 |
| 1 mms182 | <== | | |
| 2 tsip2 | AGGAGGTTCC | GTGTGGGGGT | GGCACTGGGC |
| | 2140 | 2150 | 2160 |
| 1 mms182 | <== | | |
| 2 tsip2 | CGGGCCTCCC | TCTCAGGCTC | CTTTGCTGCC |
| | 2170 | 2180 | 2190 |
| 1 mms182 | <== | | |
| 2 tsip2 | CACTTGTAAG | TTTAAATAAG | GACACCGCCC |
| | 2200 | 2210 | 2220 |
| 1 mms182 | <== | | |
| 2 tsip2 | TACACAAACC | TCACCCCTGT | CACATCCAGT |
| | 2230 | 2240 | 2250 |
| 1 mms182 | <== | | |
| 2 tsip2 | GACTCTGACC | ACTTTAGTTC | TCAAACTCTC |
| | 2260 | 2270 | 2280 |
| 1 mms182 | <== | | |
| 2 tsip2 | TCACTATTAT | CTGTGGTTGC | CGTTTCTTCC |
| | 2290 | 2300 | 2310 |
| 1 mms182 | <== | | |
| 2 tsip2 | CAAGGCCAGC | CTGGACGAAT | TTGGGGTTGC |

FIG. 8H

| | | |
|---|---|---|
| 1 mms182<br>3<br>2 tsip2 | <==<br><==<br>TCTATCCTGA GAGTTGTAAC CTCAACTTCC | 2320 2330 2340<br>2350 2360 2370 |
| 1 mms182<br>3<br>2 tsip2 | <==<br><==<br>AAAGTTTATA TTTTCTTGAA ATGATGGATC<br>2380 2390 2400 | |
| 1 mms182<br>3<br>2 tsip2 | <==<br><==<br>TATTGCTCAA CAGTCCCTGT CATCCTTAAG<br>2410 2420 2430 | |
| 1 mms182<br>3<br>2 tsip2 | <==<br><==<br>TGACTTCTGG GTTTCCCACA AATTCCTCAC<br>2440 2450 2460 | |
| 1 mms182<br>3<br>2 tsip2 | <==<br><==<br>TTTTAGACAC ACTCTAAGCT TACTTCTGGC<br>2470 2480 2490 | |
| 1 mms182<br>3<br>2 tsip2 | <==<br><==<br>CTGGATGCTT CCTCTCCCTG TCTCTCCCTT<br>2500 2510 2520 | |
| 1 mms182<br>3<br>2 tsip2 | <==<br><==<br>GCCCCACAGC GGTTCCCTGA CAGCAGACAA<br>2530 2540 2550 | |
| 1 mms182<br>3<br>2 tsip2 | <==<br><==<br>GGCAGCTCTG GGAGGTAGCT AGTATCCAAT<br>2560 2570 2580 | |
| 1 mms182<br>3<br>2 tsip2 | <==<br><==<br>AACCCAGGGG TTTCCTCATG TGATGCAAAT<br>2590 2600 2610 | |
| 1 mms182<br>3<br>2 tsip2 | <==<br><==<br>ACTACGTGTC CAACCAATCA GTGCTGTCAA<br>2620 2630 2640 | |
| 1 mms182<br>3<br>2 tsip2 | <==<br><==<br>CGGGCTGCCA TAGCTCCTTC GATGGCAAAT | |

FIG. 8I

|  | 2650 2660 2670 |
|---|---|
| 1 mms182<br>3<br>2 tsip2 | <==<br><==<br>AGGATGTGTG    CCCAAAGAAT    TAAAGCGATC<br>2680 2690 2700 |
| 1 mms182<br>3<br>2 tsip2 | <==<br><==<br>AGTGGCTGGT    G |

SEQUENCE LISTING

```
<160> NUMBER OF SEQ ID NOS: 22

<210> SEQ ID NO 1
<211> LENGTH: 230
<212> TYPE: DNA
<213> ORGANISM: TSAP 1

<400> SEQUENCE: 1
tgatcacgta cacacacaca cacagagaga gagagagaga gagagagggg gagagagaga      60
gagagagaga tcccctattc ctgacaggca gagttgaatc atgatatatg gcttaaacat     120
gtttgctatg agacagcatc acaagccagt gggcttggtg ataacaactc tgctttgtgg     180
tgcattagga catttttgag ctgctgctgc tgcaaaaaaa ataagagccg                230

<210> SEQ ID NO 2
<211> LENGTH: 143
<212> TYPE: DNA
<213> ORGANISM: TSAP 2

<400> SEQUENCE: 2
gcttggaacc aatctacaac agcgagggga agcggcttaa cactcgagag ttccgtaccc      60
gcaaaaaaaa aaatctcttg tgttttccta agcttttccc tgtgctaggg aaagatcagt     120
aagtccgtgg ttatagattg gtt                                              143
```

<210> SEQ ID NO 3
<211> LENGTH: 146
<212> TYPE: DNA
<213> ORGANISM: TSAP 3

<400> SEQUENCE: 3

```
tttttttttt tgcggggtgg gggtgtgcct gcacacatgc gtgcacgtgt gtgcttggtt        60
ttcctttaac aagccatcta cgtgtcatag cccactgttt tccccttgtg agtcaacaca      120
tagtgctgct gtggtttggg tttggt                                            146
```

<210> SEQ ID NO 4
<211> LENGTH: 202
<212> TYPE: DNA
<213> ORGANISM: TSAP 4

<400> SEQUENCE: 4

```
aactccgtcg tgggtgtggg gacctaattc cttatatttt tacaacaagc actgtacaaa        60
ctgtgccttt ccctaatgca gttatactat ttccattaag atgggtaacc ttagttaagg      120
ctttatattc actgccatgg gtaggaatgc tcacggtgaa tgggccaact tgtcatggaa      180
gaagccctca ttttcagttg gc                                                202
```

<210> SEQ ID NO 5
<211> LENGTH: 1309
<212> TYPE: DNA
<213> ORGANISM: TSAP 5

<400> SEQUENCE: 5

```
taacaaggat attcaggttc gggattggtt tcctaagcga tgatctcaac ctccacgtgg        60
aactgatttc ccaagggaca gaaatggtct ttgatctttc tgaaccactt gtcttcaaac      120
tctttggagg acgcaaccac catggcagtc agggctccgg ggcccacaca cttcacctcc      180
gaatgaagct cctctttat cttttctggg acaatgtctt cccccatagc ctcctccatc       240
aacagcaaag taccttccct aaagttgaag tccttcactt tccctgcaat ttcctgctga      300
gtcctcaagt tcttctccaa cgcgaatgat gtttgctgag actgggcgag ctgaagcagg      360
agcctggcgc ggagcaaaaa ggcgcatgct ttcctccgag cctccatctg tgcctcttcc      420
ctccgccttg ccagggaagg catattctcc tgagcactac cactcgcttc acggagagc       480
agtgcattct caggcaaggt cgtgggcaaa gacaaaagag agcctgttcc cgagtgtaca      540
gaggagggac cgacggcctt gtcacttgag gcagaactct tctgtccctg cggtgacacc      600
ctgctggcag gccgggccct ggactcaggt atgcctctgc cagcttacac cagctccacg      660
ggttgagcgg gtgcaaagca atcagcttgt gcaggcagaa gatcgtgtgc tcccggctct      720
gcaggctgga aaagacggcc aggtggaggt ggagcaccac ggtcagatgg tctgtgttgg      780
tggctttgct ttccaagtct gccgccatct ccagcgcctc ctcatgcctc ccaagtgagc      840
cagacaccga gcctggcctt cttggacatc cctttttcatg gcaaaattag tagatggtaa      900
tgttcggaga tatggagtat tcctgcaggg cttttctcgta ttcctgtcgt ctgtaggcca     960
ggtcccctct gaatttcttg agagtgagaa cttcaatatc gtcactacat tctgtctctt     1020
cataaaacca tgcggctcgc agagcttggc gcggtagggg gagggcggct cgggccggcg     1080
ctccggcctc tgctcgaaca ccgagtcctc aaattcgccg cccagcaccc agcatccggt     1140
ctccatcgcg cggaagtgca actggacctc gaaacgaggc gacacctaga gcgacgccca     1200
tcacccagcc tccaaagcgc gcgacagcag ccgcgccaag gctgccgagg caaggtagag     1260
```

```
acctgcccgg gcggccgctc gagccctata gtgagtcgta ttaggatgg         1309
```

<210> SEQ ID NO 6
<211> LENGTH: 1203
<212> TYPE: DNA
<213> ORGANISM: TSAP 6
<220> FEATURE:
<221> NAME/KEY: unsure
<222> LOCATION: (1)..(1203)
<223> OTHER INFORMATION: applicants are unsure of various bases
                        designated as "n"

<400> SEQUENCE: 6

```
gtgagtacat atcacatgta tggggtgtca ttctgagtat gtcagtttac acctgcatcc      60
caggaattag gatctcagcc acccacgcat atatcatcac ctcgctgtgc agcatccaga    120
aaagagaccc gaacccagct cagggccccc acaagccatc tccacttcca gggcctcaca    180
cgtggcttgt tttctccccc tgtgtgtggt cgccggacag catgaacttg acagccccat    240
ctttctccca gccctgcgg atcttggtga gtctgcggtt tgaggcaggg caggaggaag     300
aggcccttgg ccaggatgat tcacacaggg gcagggagca gcgtgagtgt ggaatgtggg    360
gcgggcaggt agaacttgkt agtggttttt cctncaaaag gcacgggtcc agccgtaggt    420
gagtgtgtgc attgtgctga gtatcaggc cacgaagccc agtgtggact gcacgaagct     480
gaactccttc cagttgaggg aattagcaat ggacgggagc gaggtgacag ccagcagcga    540
caacatgccc agggccagca cacccaggga caggtatatc tccatcctcc agacttcttc    600
ctcagcccag aggcggctct tgttggccag gacctgcttc acagccagat tgaccaggtc    660
gtaggcggtg ggagcggcgc agcggcaggc agaagctgta gagagcgtgc agcatcgcga    720
agaagaagct gagcagcccg atctgcttgc gatgctgcag ccagtggtcc agccagtctg    780
ggaagcgctg gtacttggtc ccctccgca gctgaagcgc agctgccagc acccgggca     840
ggtacactag ggacagcagc acataagcca cacagggtag tgtggtgttg accacagaca    900
agggcatctt gtaaaacttg ttctcatctt tccgaatgtn tggctgtana acgtcccgga    960
tgaaattgta ggtgtanaan cacacaaaga ccccagtgcc caggaaggtg ggccccttcc   1020
agaatggaag gaagcncagg ggtttngctt ctacctccct cnctgaaggc canggatcca   1080
tntccagggg ttnaaaccat ngggcgtgca tctctgaaaa tggtcncttg gnttctggtk   1140
gatcamtgca ataacncct gcctgttccn tcccttgggg ccacccntntn ggggccatgc   1200
caa                                                                 1203
```

<210> SEQ ID NO 7
<211> LENGTH: 140
<212> TYPE: DNA
<213> ORGANISM: TSAP 7

<400> SEQUENCE: 7

```
gcccatccag tcattcttta tttcagtgtg tgaaagcctc ctacgcattt tcccccaaat     60
taatttttaa tccattttca aaccagcctt tactgtggcc ttttctgcta tttttgatat    120
atgttagcac gtgtgcatag                                                140
```

<210> SEQ ID NO 8
<211> LENGTH: 257
<212> TYPE: DNA
<213> ORGANISM: TSAP 8
<220> FEATURE:
<221> NAME/KEY: unsure

```
<222> LOCATION: (1)..(257)
<223> OTHER INFORMATION: applicants are unsure of various bases
                        designated as "n"

<400> SEQUENCE: 8
cacgtnaaag taccacatcc nccccattg gtagatattg anagagtata tanataggnc    60
gaagcacaat ctcttccctt cctntgtaca cctcanaccc agtgacttcc naccnaagcn  120
cntgantgtn tttgtngata tgagtgtctg ngtgtgtgna tntgcgtctc acatgtatgg  180
gacgaccnac cccaccccca gcggccttca ngcacaatng aggacgccta tngtggatac  240
gngcatcggt aaanagc                                                 257

<210> SEQ ID NO 9
<211> LENGTH: 111
<212> TYPE: DNA
<213> ORGANISM: TSIP 1

<400> SEQUENCE: 9 ggaggggtc tagctttctc tttagttatc actctgaggt gctcaggtca cagagaaggc   60
acttaattgg gaaggtcatc tgattccggc catcttctct cccttacca a            111

<210> SEQ ID NO 10
<211> LENGTH: 2681
<212> TYPE: DNA
<213> ORGANISM: TSIP 2

<400> SEQUENCE: 10
caccggtgag acctctaggg cggggcctag gacgacctgc tccgtgggcc gcgagtattc   60
gtcggaaaca aaacagcggc agctgagcg gaaacctagg ctgcgagccg gccgcccggg   120
cgcggagaga gaaggaacca acacaagaca gcagcccttc gaggtcttta ggcagcttgg   180
aggagaacac atgagagaaa gaatcccaag aggttttgtt ttctttgaga aggtatttct   240
gtccagctgc tccaatgaca gagatacctg cacctttgtc ctacttccag aatgcccaga   300
tgtctgagga cagccactcc agcagcgcca tccggagcca gaatgacagc caagaacggc   360
agcagcagca tgacaggcag agacttgaca accctgagcc aatatctaat gggcggcccc   420
agagtaactc aagacaggtg gtggaacaag atgaggagga agacgaagag ctgacattga   480
aatatggagc caagcatgtc atcatgctct tgtccccgt gaccctctgc atggtcgtcg   540
tcgtggccac catcaaatca gtcagcttct ataccggaa ggacggtcag ctaatctaca   600
ccccattcac agaagacact gagactgtag gccaaagagc cctgcactcg atcctgaatg   660
cggccatcat gatcagtgtc attgtcatta tgaccatcct cctggtggtc ctgtataaat   720
acaggtgcta caaggtcatc cacgcctggc ttattatttc atctctgttg ttgctgttct   780
ttttttcgtt catttactta ggggaagtat ttaagaccta caatgtcgcc gtggactacg   840
ttacagtagc actcctaatc tggaattttg gtgtggtcgg gatgattgcc atccactgga   900
aaggccccct tcgactgcag caggcgtatc tcattatgat cagtgccctc atggccctgg   960
tatttatcaa gtacctcccc gaatggaccg catggctcat cttggctgtg atttcagtat   1020 atgattttggt ggctgttta tgtcccaaag gcccacttcg tatgctggtt gaaacagctc   1080
aggaaagaaa tgagactctc tttccagctc ttatctattc ctcaacaatg gtgtggttgg   1140
tgaatatggc tgaaggagac ccagaagccc aaaggagggt acccaagaac cccaagtata   1200
acacacaaag agcggagaga gagacacagg acagtggttc tgggaacgat gatggtggct   1260
tcagtgagga gtgggaggcc caaagagaca gtcacctggg gcctcatcgc tccactcccg   1320
```

-continued

```
agtcaagagc tgctgtccag gaactttctg ggagcattct aacgagtgaa gacccggagg    1380
aaagaggagt aaaacttgga ctgggagatt tcattttcta cagtgttctg gttggtaagg    1440
cctcagcaac cgccagtgga gactggaaca caaccatagc ctgctttgta gccatactga    1500
tcggcctgtg ccttacatta ctcctgctcg ccattttcaa gaaagcgttg ccagccctcc    1560
ccatctccat caccttcggg ctcgtgttct acttcgccac ggattacctt gtgcagccct    1620
tcatggacca acttgcattc catcagtttt atatctagcc tttctgcagt tagaacatgg    1680
atgtttcttc tttgattatc aaaaacacaa aaacagagag caagcccgag gaggagactg    1740
gtgactttcc tgtgtcctca gctaacaaag gcaggactcc agctggactt ctgcagcttc    1800
cttccgagtc tccctagcca cccgcactac tggactgtgg aaggaagcgt ctacagagga    1860
acggtttcca acatccatcg ctgcagcaga cggtgtccct cagtgacttg agagacaagg    1920
acaaggaaat gtgctgggcc aaggagctgc cgtgctctgc tagctttgac cgtgggcatg    1980
gagatttacc cgcactgtga actctctaag gtaaacaaag tgaggtgaac caaacagagc    2040
tgccatyctt ccacaccatg ttggaaataa aaccgtccta gctggaaccc ttactgtccc    2100
aggaggttcc gtgtgggggt ggcactgggc cgggcctccc tctcaggctc ctttgctgcc    2160
cacttgtaag tttaaataag gacaccgccc tacacaaacc tcacccctgt cacatccagt    2220
gactctgacc actttagttc tcaaactctc tcactattat ctgtggttgc cgtttcttcc    2280
caaggccagc ctggacgaat ttgggggttgc tctatcctga gagttgtaac ctcaacttcc    2340
```

```
aaagtttata ttttcttgaa atgatggatc tattgctcaa cagtccctgt catccttaag    2400
tgacttctgg gtttcccaca aattcctcac ttttagacac actctaagct tacttctggc    2460
ctggatgctt cctctccctg tctctcccct gccccacagc ggttccctga cagcagacaa    2520
ggcagctctg ggaggtagct agtatccaat aacccagggg tttcctcatg tgatgcaaat    2580
actacgtgtc caaccaatca gtgctgtcaa cgggctgcca tagctccttc gatggcaaat    2640
aggatgtgtg cccaaagaat taaagcgatc agtggctggt g                       2681
```

<210> SEQ ID NO 11
<211> LENGTH: 1884
<212> TYPE: DNA
<213> ORGANISM: TSAP 3
<220> FEATURE:
<221> NAME/KEY: CDS
<222> LOCATION: (1)..(846)

<400> SEQUENCE: 11

```
atg agc cgt cag act gct aca gca tta cct acc ggt acc tcg aag tgt        48
Met Ser Arg Gln Thr Ala Thr Ala Leu Pro Thr Gly Thr Ser Lys Cys
 1               5                  10                  15 cca cca tcc cag agg gtg cct gcc ctg act ggc aca act gca tcc aac        96
Pro Pro Ser Gln Arg Val Pro Ala Leu Thr Gly Thr Thr Ala Ser Asn
            20                  25                  30 aat gac ttg gcg agt ctt ttt gag tgt cca gtc tgc ttt gac tat gtg       144
Asn Asp Leu Ala Ser Leu Phe Glu Cys Pro Val Cys Phe Asp Tyr Val
        35                  40                  45 tta ccg ccc att ctt caa tgt cag agt ggc cat ctt gtt tgt agc aac       192
Leu Pro Pro Ile Leu Gln Cys Gln Ser Gly His Leu Val Cys Ser Asn
    50                  55                  60 tgt cgc cca aag ctc aca tgt tgt cca act tgc cgg ggc cct ttg gga       240
Cys Arg Pro Lys Leu Thr Cys Cys Pro Thr Cys Arg Gly Pro Leu Gly
65                  70                  75                  80 tcc att cgc aac ttg gct atg gag aaa gtg gct aat tca gta ctt ttc       288
```

```
Ser Ile Arg Asn Leu Ala Met Glu Lys Val Ala Asn Ser Val Leu Phe
            85                  90                  95 ccc tgt aaa tat gcg tct tct gga tgt gaa ata act ctg cca cac aca      336
Pro Cys Lys Tyr Ala Ser Ser Gly Cys Glu Ile Thr Leu Pro His Thr
            100                 105                 110 gaa aaa gca gac cat gaa gag ctc tgt gag ttt agg cct tat tcc tgt      384
Glu Lys Ala Asp His Glu Glu Leu Cys Glu Phe Arg Pro Tyr Ser Cys
            115                 120                 125 ccg tgc cct ggt gct tcc tgt aaa tgg caa ggc tct ctg gat gct gta      432
Pro Cys Pro Gly Ala Ser Cys Lys Trp Gln Gly Ser Leu Asp Ala Val
            130                 135                 140 atg ccc cat ctg atg cat cag cat aag tcc att aca acc cta cag gga      480
Met Pro His Leu Met His Gln His Lys Ser Ile Thr Thr Leu Gln Gly
145                 150                 155                 160 gag gat ata gtt ttt ctt gct aca gac att aat ctt cct ggt gct gtt      528
Glu Asp Ile Val Phe Leu Ala Thr Asp Ile Asn Leu Pro Gly Ala Val
                165                 170                 175 gac tgg gtg atg atg cag tcc tgt ttt ggc ttt cac ttc atg tta gtc      576
Asp Trp Val Met Met Gln Ser Cys Phe Gly Phe His Phe Met Leu Val
                180                 185                 190 tta gag aaa cag gaa aaa tac gat ggt cac cag cag ttc ttc gca atc      624
Leu Glu Lys Gln Glu Lys Tyr Asp Gly His Gln Gln Phe Phe Ala Ile
            195                 200                 205 gta cag ctg ata gga aca cgc aag caa gct gaa aat ttt gct tac cga      672
Val Gln Leu Ile Gly Thr Arg Lys Gln Ala Glu Asn Phe Ala Tyr Arg
            210                 215                 220 ctt gag cta aat ggt cat agg cga cga ttg act tgg gaa gcg act cct      720
Leu Glu Leu Asn Gly His Arg Arg Arg Leu Thr Trp Glu Ala Thr Pro
225                 230                 235                 240 cga tct att cat gaa gga att gca aca gcc att atg aat agc gac tgt      768
Arg Ser Ile His Glu Gly Ile Ala Thr Ala Ile Met Asn Ser Asp Cys
                245                 250                 255 cta gtc ttt gac cca gca ttg cac agc ttt ttg cag aca aat ggc aat      816
Leu Val Phe Asp Pro Ala Leu His Ser Phe Leu Gln Thr Asn Gly Asn
                260                 265                 270 tta ggc atc aat gta act att tcc atg tgt tgaaatggca atcaaacatt        866
Leu Gly Ile Asn Val Thr Ile Ser Met Cys
            275                 280 ttctggccag tgtttaaaac ttcagtttca cagaaaataa ggcacccatc tgtctgccaa    926
cctaaaactc tttcggtagg tagaagctcg acatgaaggc caataaaaag aaagactgct    986
aaatacagga aacagttcca tgtagtaaca ctaatatatt taaaaataag tcaacagtaa   1046
accactgaaa aaatatatgt atatacaccc aagatgggca tcttttgtat taagaaagga   1106
agcattgtaa aataattctg agttttgtgt tgttgtaga ttgattgtat tgttgaaaaa    1166
gtttgttttt gcgtgggagt gtgtgcctgc gtgggtgtgt gcgtgtttgg gtttttttcc   1226
tttaactgac aagccatctt gagtggtcat gggccactgc ttttcccttt gtgagtcaat   1286
acatagtgct gctgtaagcc gtttttgtgt gtatttgcta atttttatta attttagttt   1346
ttcattaaat aaatttgact tttctgtaat tcaggttttt cctttttttg taccatttta   1406
aagttagtat cttttgatat ggcatatttg tttatggtaa aaaatttata acgggttcaa   1466
tattttcttt tcccccatta atcaagtcca ttggaaatat tttaaaacca gcctatttg    1526 gtgaacccat gagttcccag aaagtaaagg tgacacccgg aaaaataatc caaaagccta   1586
tttaaagcca cctataaggt gccccccttt cctgtcttcc tacagatgag tcacacctt    1646 gagccttaac ctttgaaagg ttagagaata aattgatttt tataaatact gcaaatccag   1706
```

```
gcttttgttt cctttttcca gatatccttg gacaaatcac atattttaaa atttgttctt      1766
gtatttattg gttttgcaga agaaggcatc gtcatgcaca gtatttgtaa ttaaaagcaa      1826
attcatttgt ttaaaaaggc agtttgcaaa aaatgttttt ggtcttttat aattctca        1884
```

<210> SEQ ID NO 12
<211> LENGTH: 282
<212> TYPE: PRT
<213> ORGANISM: TSAP 3

<400> SEQUENCE: 12

```
Met Ser Arg Gln Thr Ala Thr Ala Leu Pro Thr Gly Thr Ser Lys Cys
 1               5                  10                  15

Pro Pro Ser Gln Arg Val Pro Ala Leu Thr Gly Thr Thr Ala Ser Asn
            20                  25                  30

Asn Asp Leu Ala Ser Leu Phe Glu Cys Pro Val Cys Phe Asp Tyr Val
        35                  40                  45

Leu Pro Pro Ile Leu Gln Cys Gln Ser Gly His Leu Val Cys Ser Asn
    50                  55                  60

Cys Arg Pro Lys Leu Thr Cys Cys Pro Thr Cys Arg Gly Pro Leu Gly
65                  70                  75                  80

Ser Ile Arg Asn Leu Ala Met Glu Lys Val Ala Asn Ser Val Leu Phe
                85                  90                  95

Pro Cys Lys Tyr Ala Ser Ser Gly Cys Glu Ile Thr Leu Pro His Thr
            100                 105                 110

Glu Lys Ala Asp His Glu Glu Leu Cys Glu Phe Arg Pro Tyr Ser Cys
        115                 120                 125

Pro Cys Pro Gly Ala Ser Cys Lys Trp Gln Gly Ser Leu Asp Ala Val
    130                 135                 140

Met Pro His Leu Met His Gln His Lys Ser Ile Thr Thr Leu Gln Gly
145                 150                 155                 160

Glu Asp Ile Val Phe Leu Ala Thr Asp Ile Asn Leu Pro Gly Ala Val
                165                 170                 175

Asp Trp Val Met Met Gln Ser Cys Phe Gly Phe His Phe Met Leu Val
            180                 185                 190

Leu Glu Lys Gln Glu Lys Tyr Asp Gly His Gln Gln Phe Phe Ala Ile
        195                 200                 205

Val Gln Leu Ile Gly Thr Arg Lys Gln Ala Glu Asn Phe Ala Tyr Arg
    210                 215                 220

Leu Glu Leu Asn Gly His Arg Arg Leu Thr Trp Glu Ala Thr Pro
225                 230                 235                 240

Arg Ser Ile His Glu Gly Ile Ala Thr Ala Ile Met Asn Ser Asp Cys
                245                 250                 255

Leu Val Phe Asp Pro Ala Leu His Ser Phe Leu Gln Thr Asn Gly Asn
            260                 265                 270

Leu Gly Ile Asn Val Thr Ile Ser Met Cys
        275                 280
```

<210> SEQ ID NO 13
<211> LENGTH: 287
<212> TYPE: DNA
<213> ORGANISM: RAT

<400> SEQUENCE: 13

```
cttcttctac ttaacaattt gactattgaa tttctttggc caaccaaaag tagctatgta       60
cacacacaca cacacacaca cacacacaca cacacacaca cacagaaatc ccctattcct      120
```

```
gacaggcaga gttgaaccat aatccacaac ttaaacatgt tggctagggg acagcatcac      180
aagccagtgg gcttggtgat aacaactctg ctttgtggtg cattaggaca tgttcgagct      240
cctgctggaa aaggaaaatt agtgcattag tactttaatg gcaagcc                    287

<210> SEQ ID NO 14
<211> LENGTH: 170
<212> TYPE: DNA
<213> ORGANISM: HUMAN

<400> SEQUENCE: 14
cccctgagcc catctacaat agcgagggga agcggcttaa caccccgagag ttccgcaccc     60 gcaaaaagct ggaagaggag cggcacaacc tcatcacaga gatggttgca ctcaatccgg     120
atttcaagcc acctgcagat tacaaacctc cagcaacacg tgtgagtgat                170

<210> SEQ ID NO 15
<211> LENGTH: 240
<212> TYPE: DNA
<213> ORGANISM: MOUSE

<400> SEQUENCE: 15
ttgtaaaata tttctgaact ttgtatttgt tgtagattga ttgtattgtt gacaattttt      60
cggggtgggg gtgtgcctgc acacatgcgt gcacgtgtgt gcttggtttt cctttaacaa     120
gccatctacg tgtcatagcc cactcttttc cccttgtgag tcaacacata gtgctgctgt     180
ggttttggtt tggtttgctt ttggtttttg atgtgtgtgt atttgataat ttttattcta     240

<210> SEQ ID NO 16
<211> LENGTH: 1636
<212> TYPE: DNA
<213> ORGANISM: MOUSE
<220> FEATURE:
<221> NAME/KEY: unsure
<222> LOCATION: (1)..(1636)
<223> OTHER INFORMATION: applicants are unsure of various bases
                designated as "n"

<400> SEQUENCE: 16
accanacanc ggcagctgag gcggaaacct aggctgcgag ccggccgccc gggcgcggag      60
agagaaggaa ccaacacaag acagcagccc ttcgaggtct taggcagct tggaggagaa     120 cacatgagag aaagaatccc aagaggtttt gttttctttg agaaggtatt tctgtccagt     180
tgctccaatg acagagatac ctgcaccttt gtcctacttc cagaatgccc agatgtctga     240
ggacagccac tccagcagcg ccatccggag ccagaatgac agccagaac ggcagcagca     300 gcatgacagg cagagacttg acaaccctga gccaatatct aatgggcggc cccagagtaa     360
ctcaagacag gtggtggaac aagatgagga ggaagacgaa gagctgacat tgaaatatgg     420
agccaagcat gtcatcatgc tctttgtccc ccgtgaccct ctgcatggtc gtcgtcgtgg     480
ccaccatcaa atcagtcagc ttctataccc ggaaggacgg tcagctaatc tacaccccat     540
tcacagaaga cactgagact gtaggccaaa gagccctgca ctcgatcctg aatgcggcca     600
tcatgatcag tgtcattgtc attatgacca tcctcctggt ggtcctgtat aaatacaggt     660
gctacaaggt catccacgcc tggcttatta tttcatctct gttgttgctg ttcttttttt     720
cgttcattta cttaggggaa gtatttaaga cctacaatgt cgccgtggac tacgttacag     780
tagcactcct aatctggaat tttggtgtgg tcggatgat tgccatccac tggaaaggcc     840
cccttcgact gcagcaggcg tatctcatta tgatcagtgc cctcatggcc ctggtattta     900
```

```
tcaagtacct cccgaatgg accgcatggc tcatcttggc tctgatttca gtatatgatt    960
tggtggctgt tttatgtccc aaaggcccac ttcgtatgct ggttgaaaca gctcaggaaa  1020
gaaatgagac tctctttcca gctcttatct attcctcaac aatggtgtgg ttggtgaata  1080
tggctgaagg agacccagaa gcccaaagga gggtacccaa gaaccccaag tataacacac  1140
aaagagcgga gagagagaca caggacagtg ttctgggaac gatgatggt ggcttcagtg   1200
aggagtggga ggcccaaaga gacagtcacc tggggcctca tcgctccact ccccgagtca  1260
agagctgctg tccaggaact ttctgggagc attctaacga gtgaagaccc ggaggaaaga  1320
ggagtaaaac ttggactggg agatttcatt ttctacagtg ttctggttgg taaggcctca  1380
gcaaccgcca gtggagactg aacacaacc atagcctgct tgtagccat actgatcggc    1440
ctgtgcctta cattactcct gctcgccatt ttcaagaaag cgttgccagc cctccccatc  1500
tccatcacct tcgggctcgt gttctacttc gccacggatt accttgtgca gcccttcatg  1560
gaccaacttg cattccatca gttttgagat ttacccgcac tgtgaactct ctaaggtaaa  1620
caaagtgagg tgaacc                                                  1636
```

<210> SEQ ID NO 17
<211> LENGTH: 282
<212> TYPE: PRT
<213> ORGANISM: HUMAN

<400> SEQUENCE: 17

```
Met Ser Arg Gln Thr Ala Thr Ala Leu Pro Thr Gly Thr Ser Lys Cys
1               5                   10                  15

Pro Pro Ser Gln Arg Val Pro Ala Leu Thr Gly Thr Thr Ala Ser Asn
            20                  25                  30

Asn Asp Leu Ala Ser Leu Phe Glu Cys Pro Val Cys Phe Asp Tyr Val
        35                  40                  45

Leu Pro Pro Ile Leu Gln Cys Gln Ser Gly His Leu Val Cys Ser Met
    50                  55                  60

Cys Arg Pro Lys Leu Thr Cys Cys Pro Thr Cys Arg Gly Pro Leu Gly
65                  70                  75                  80

Ser Ile Arg Asn Leu Ala Met Glu Lys Val Ala Asn Ser Val Leu Phe
                85                  90                  95

Pro Cys Lys Tyr Ala Ser Ser Gly Cys Glu Ile Thr Leu Pro His Thr
            100                 105                 110

Glu Lys Ala Asp His Glu Glu Leu Cys Glu Phe Arg Pro Tyr Ser Cys
        115                 120                 125

Pro Cys Pro Gly Ala Ser Cys Lys Trp Gln Gly Ser Leu Asp Ala Val
    130                 135                 140

Met Pro His Leu Met His Gln His Lys Ser Ile Thr Thr Leu Gln Gly
145                 150                 155                 160

Glu Asp Ile Val Phe Leu Ala Thr Asp Ile Asn Leu Pro Gly Ala Val
                165                 170                 175

Asp Trp Val Met Met Gln Ser Cys Phe Gly Phe His Phe Met Leu Val
            180                 185                 190

Leu Glu Lys Gln Glu Lys Tyr Asp Gly His Gln Gln Phe Phe Ala Ile
        195                 200                 205

Val Gln Leu Ile Gly Thr Arg Lys Gln Ala Glu Asn Phe Ala Tyr Arg
    210                 215                 220

Leu Glu Leu Asn Gly His Arg Arg Arg Leu Thr Trp Glu Ala Thr Pro
225                 230                 235                 240
```

```
Arg Ser Ile His Glu Gly Ile Ala Thr Ala Ile Met Asn Ser Asp Cys
                245                 250                 255

Leu Val Phe Asp Thr Ser Ile Ala Gln Leu Phe Ala Glu Asn Gly Asn
            260                 265                 270

Leu Gly Ile Met Val Thr Ile Ser Met Cys
        275                 280

<210> SEQ ID NO 18
<211> LENGTH: 282
<212> TYPE: PRT
<213> ORGANISM: MOUSE

<400> SEQUENCE: 18

Met Ser Arg Gln Thr Ala Thr Ala Leu Pro Thr Gly Thr Ser Lys Cys
  1               5                  10                  15

Pro Pro Ser Gln Arg Val Pro Ala Leu Thr Gly Thr Thr Ala Ser Asn
             20                  25                  30

Asn Asp Leu Ala Ser Leu Phe Glu Cys Pro Val Cys Phe Asp Tyr Val
             35                  40                  45

Leu Pro Pro Ile Leu Gln Cys Gln Ser Gly His Leu Val Cys Ser Met
         50                  55                  60

Cys Arg Pro Lys Leu Thr Cys Cys Pro Thr Cys Arg Gly Pro Leu Gly
 65                  70                  75                  80

Ser Ile Arg Asn Leu Ala Met Glu Lys Val Ala Asn Ser Val Leu Phe
                 85                  90                  95

Pro Cys Lys Tyr Ala Ser Ser Gly Cys Glu Ile Thr Leu Pro His Thr
            100                 105                 110

Glu Lys Ala Glu His Glu Glu Leu Cys Glu Phe Arg Pro Tyr Ser Cys
        115                 120                 125

Pro Cys Pro Gly Ala Ser Cys Lys Trp Gln Gly Ser Leu Asp Ala Val
    130                 135                 140

Met Pro His Leu Met His Gln His Lys Ser Ile Thr Thr Leu Gln Gly
145                 150                 155                 160

Glu Asp Ile Val Phe Leu Ala Thr Asp Ile Asn Leu Pro Gly Ala Val
                165                 170                 175

Asp Trp Val Met Met Gln Ser Cys Phe Gly Phe His Phe Met Leu Val
            180                 185                 190

Leu Glu Lys Gln Glu Lys Tyr Asp Gly His Gln Gln Phe Phe Ala Ile
        195                 200                 205

Val Gln Leu Ile Gly Thr Arg Lys Gln Ala Glu Asn Phe Ala Tyr Arg
    210                 215                 220

Leu Glu Leu Asn Gly His Arg Arg Leu Thr Trp Glu Ala Thr Pro
225                 230                 235                 240

Arg Ser Ile His Glu Gly Ile Ala Thr Ala Ile Met Asn Ser Asp Cys
                245                 250                 255

Leu Val Phe Asp Thr Ser Ile Ala Gln Leu Phe Ala Glu Asn Gly Asn
            260                 265                 270

Leu Gly Ile Met Val Thr Ile Ser Met Cys
        275                 280

<210> SEQ ID NO 19
<211> LENGTH: 282
<212> TYPE: PRT
<213> ORGANISM: MOUSE

<400> SEQUENCE: 19
```

-continued

```
Met Ser Arg Gln Ala Ala Thr Ala Leu Ser Thr Gly Thr Ser Lys Cys
 1               5                  10                  15

Pro Pro Ser Gln Arg Val Pro Ala Leu Thr Asp Thr Thr Ala Ser Asn
            20                  25                  30

Asn Asp Leu Ala Ser Leu Phe Glu Cys Pro Val Cys Phe Asp Tyr Val
            35                  40                  45

Leu Pro Pro Ile Leu Gln Cys Gln Ser Gly His Leu Val Cys Ser Asn
        50                  55                  60

Cys Arg Pro Lys Leu Thr Cys Cys Pro Thr Cys Arg Gly Pro Leu Gly
 65                  70                  75                  80

Ser Ile Arg Asn Leu Ala Met Glu Lys Val Ala Asn Ser Val Leu Phe
                85                  90                  95

Pro Cys Lys Tyr Ser Ala Ser Gly Cys Glu Ile Thr Leu Pro His Thr
            100                 105                 110

Lys Lys Ala Glu His Glu Leu Cys Glu Phe Arg Pro Tyr Ser Cys
            115                 120                 125

Pro Cys Pro Gly Ala Ser Cys Lys Trp Gln Gly Ser Leu Asp Ala Val
            130                 135                 140

Met Pro His Leu Met His Gln His Lys Ser Ile Thr Thr Leu Gln Gly
145                 150                 155                 160

Glu Asp Ile Val Phe Leu Ala Thr Asp Ile Asn Leu Pro Gly Ala Val
                165                 170                 175

Asp Trp Val Met Met Gln Ser Cys Phe Gly Phe His Phe Met Leu Val
            180                 185                 190

Leu Glu Lys Gln Glu Lys Tyr Asp Gly His Gln Gln Phe Phe Ala Ile
            195                 200                 205

Val Gln Leu Ile Gly Thr Arg Lys Gln Ala Glu Met Phe Ala Tyr Arg
        210                 215                 220

Leu Glu Leu Asn Gly His Arg Arg Leu Thr Trp Glu Ala Thr Pro
225                 230                 235                 240

Arg Ser Ile His Glu Gly Ile Ala Thr Ala Ile Met Asn Ser Asp Cys
                245                 250                 255

Leu Val Phe Asp Thr Ser Ile Ala Gln Leu Phe Ala Glu Asn Gly Asn
            260                 265                 270

Leu Gly Ile Met Val Thr Ile Ser Met Cys
        275                 280
```

<210> SEQ ID NO 20
<211> LENGTH: 314
<212> TYPE: PRT
<213> ORGANISM: DROSINA

<400> SEQUENCE: 20

```
Met Ser Asn Lys Ile Met Pro Lys Arg Glu Pro Thr Ala Ala Ala
 1               5                  10                  15

Ala Gly Ala Gly Ala Thr Gly Val Ala Thr Asn Thr Ser Thr Ser Thr
            20                  25                  30

Gly Ser Ser Ser Ala Gly Asn Thr Ser Ser Ala Met Thr Ser Ser Ser
        35                  40                  45

Ser Ser Ser Ser Leu Ser Ser Ala Gly Gly Gly Ala Gly Met Ser
     50                  55                  60

Ala Asp Leu Thr Ser Leu Phe Glu Cys Pro Val Cys Phe Asp Tyr Val
 65                  70                  75                  80

Leu Pro Pro Ile Leu Gln Cys Ser Ser Gly His Leu Val Cys Val Ser
```

-continued

```
                        85                  90                  95
Cys Arg Ser Lys Leu Thr Cys Cys Pro Thr Cys Arg Gly Pro Leu Ala
                100                 105                 110
Met Ile Arg Asn Leu Ala Met Glu Lys Val Ala Ser Asn Val Lys Phe
                115                 120                 125
Pro Cys Lys His Ser Gly Tyr Gly Cys Thr Ala Ser Leu Val Tyr Thr
                130                 135                 140
Glu Lys Thr Glu His Glu Glu Thr Cys Glu Cys Arg Pro Tyr Leu Cys
145                 150                 155                 160
Pro Cys Pro Gly Ala Ser Cys Lys Trp Gln Gly Pro Leu Asp Leu Val
                165                 170                 175
Met Gln His Leu Met Met Ser His Lys Ser Ile Thr Thr Leu Gln Gly
                180                 185                 190
Glu Asp Ile Val Phe Leu Ala Thr Asp Ile Asn Leu Pro Gly Ala Val
                195                 200                 205
Asp Trp Val Met Met Gln Ser Cys Phe Gly His His Phe Met Leu Val
        210                 215                 220
Leu Glu Lys Gln Glu Lys Tyr Asp Gly His Gln Gln Phe Phe Ala Ile
225                 230                 235                 240
Val Gln Leu Ile Gly Ser Arg Lys Glu Ala Glu Asn Phe Val Tyr Arg
                245                 250                 255
Leu Glu Leu Asn Gly Asn Arg Arg Leu Thr Trp Glu Ala Met Pro
                260                 265                 270
Arg Ser Ile His Glu Gly Val Ala Ser Ala Ile His Met Ser Asp Cys
                275                 280                 285
Leu Val Phe Asp Thr Ser Ile Ala Gln Leu Phe Ala Asp Met Gly Met
        290                 295                 300
Leu Gly Ile Met Val Thr Ile Ser Leu Val
305                 310

<210> SEQ ID NO 21
<211> LENGTH: 20
<212> TYPE: DNA
<213> ORGANISM: primer

<400> SEQUENCE: 21
cagtaaacca ctgaaaaacc                                               20

<210> SEQ ID NO 22
<211> LENGTH: 19
<212> TYPE: DNA
<213> ORGANISM: primer

<400> SEQUENCE: 22
caaaccaaac caaaaccac                                                19
```

US 6,503,502 B1

NUCLEOTIDE SEQUENCES, PROTEINS, DRUGS AND DIAGNOSTIC AGENTS OF USE IN TREATING CANCER

CROSS REFERENCE TO RELATED APPLICATIONS

This application is a divisional application of U.S. Ser. No. 09/134,873, filed Aug. 17, 1998 now abandoned which in turn, is a continuation-in-part application of U.S. Ser. No. 09/091,647, filed Jun. 22, 1998, abandoned Jul. 29, 1999, which in turn is a 371 of PCT/FR96/02061, filed Dec. 20, 1996. This application also claims foreign priority to French Patent Application No. 96 04853, filed Apr. 18, 1996 and French Patent Application No. 95 15146, filed Dec. 20, 1995.

FIELD OF THE INVENTION

The present invention relates to the demonstration of genes which are involved in the molecular pathways of tumor suppression and to the use of the genes which have thus been demonstrated for treating certain genetic malfunctions, in particular cancers.

BACKGROUND OF THE INVENTION

The present invention was made possible by isolating cDNA which corresponded to the messenger RNAs which are expressed or repressed during the process of apoptosis which is induced by the p53 suppressor gene.

A global analysis of the molecular events which take place during the cell cycle at the time of development and cell apoptosis is required in order to better understand the importance of the p53 gene in the process of tumor suppression or, on the contrary, of canceration.

The transformation of a normal cell into a tumor cell is a process which takes place in several stages and which requires a sequence of molecular events. At the physiological level, these events find expression in the tumor cell becoming independent of external signals and in an internal deregulation which leads to uncontrolled growth.

Two groups of genes are responsible for this so-called "malignant" transformation; on the one hand oncogenes and, on the other hand, suppressor genes or anti-oncogenes. Because of their deregulation in cancer (resulting most frequently from a mutation or a translocation), oncogenes induce a positive signal which promotes neoplastic growth. By contrast, the suppressor genes are unable, either because they have been deleted, because they are not being expressed due to mutation of the promoter, for example, or because of mutations which modify the structure and function of the protein, to supply, in the cancer, the signal which would normally retard this abnormal growth. As a consequence, malfunction of the suppressor genes contributes to neoplastic transformation.

SUMMARY OF THE INVENTION

The object of the present invention is to isolate genes which normally play a part in tumor suppression and any possible malfunctions of which can then be monitored and treated.

In particular, isolation of these genes makes it possible to carry out a gene replacement therapy or else to synthesize protein or non-protein pharmacological agents which, directly or indirectly, induce activation and expression of these genes by acting on the promoters, or else to synthesize pharmacological agents which mimic the physiological effect of these suppressor genes.

The final objective is either to inhibit tumor growth or, even better, induce the apoptotic process in these tumor cells, that is to cause the tumor cells to "commit suicide".

Thus, in one embodiment the invention relates to an isolated DNA molecule comprising a sequence selected from the group consisting of:

(a) a nucleotide sequence of one of SEQ ID Nos. 4 to 11,
(b) a nucleotide sequence that hybridizes with one of the sequences of
(a), and
(c) a nucleotide sequence that is at least 80% homologous with a
sequence of either (a) or (b). Expression of this DNA molecule may activate cell apoptosis and/or tumor suppression.

In another embodiment, the invention relates to an isolated DNA molecule comprising a sequence selected from the group consisting of:

(a) a nucleotide sequence of one of SEQ ID Nos. 1 or 3;
(b) a nucleotide sequence that hybridizes with one of the sequences of
(a), and
(c) a sequence that is at least 80% homologous with a sequence of either
(a) or (b). Tumor suppression induces expression of this DNA molecule.

In another embodiment, the invention relates to an isolated DNA molecule comprising a sequence selected from the group consisting of:

(a) SEQ ID No. 2,
(b) a nucleotide sequence that hybridizes with SEQ ID No. 2, and
(c) a nucleotide sequence that is at least 80% homologous with either (a) or (b); wherein cell apoptosis induces expression of this DNA molecule.

In a preferred embodiment, the DNA molecule of this invention is SEQ ID No. 11 or fragment thereof.

In yet another embodiment, the invention relates to a biologically functional vector comprising one of the above described DNA molecules. Another embodiment relates to a host cell stably transformed with this vector. In yet another embodiment, the invention relates to a protein obtained by culturing the host cell under appropriate nutrient conditions so as to allow the cell to express the protein.

In another embodiment, the invention relates to a pharmaceutical composition comprising the above described vector and a pharmaceutically acceptable carrier. Another embodiment relates to a method of preventing tumorigenesis, the method comprising contacting cells with a tumorigenesis inhibiting amount of the pharmaceutical composition. In a preferred embodiment, the pharmaceutical composition comprises the DNA SEQ ID NO. 11 or TSAP 3.

In other embodiments, the invention relates to a DNA probe or a PCR amplification primer comprising a nucleotide sequence selected from the group consisting of SEQ ID No. 1–11, or a fragment thereof.

DETAILED DESCRIPTION OF THE INVENTION

The present invention relates to demonstrating genes which are involved in this apoptosis, particularly TSAP 3, which has been discovered to directly activate apoptosis. Thus, each cell contains within itself a program of physiological death. This is also a physiological process which is involved in development for the purpose of maintaining homeostasis of the body and of preventing abnormal cell proliferations from becoming established even if, for all that, they are not malignant in nature.

One of the most important suppressor genes involved in apoptosis is the p53 gene. In its normal function, this gene controls cell growth and the apoptotic process; in particular, it is this gene which blocks cell growth and which is responsible for inducing the apoptotic process in order to avoid the development of a cancer. Thus, it has been demonstrated that mice which are nullizygous for p53 are much more sensitive to the formation of tumors. The fact has also been demonstrated that, in cancers, the p53 gene is very often altered and leads to the production of proteins which are unable to serve as a vehicle for the apoptotic message.

It is this distinctive feature which has been employed within the context of the present invention.

Thus, the present invention is based on the observation that it is not possible, or that it at least appears very difficult, to institute a direct replacement therapy when the p53 gene is malfunctioning. Thus, when p53 is mutated as it is in cancer, it nullifies the physiological effect of the normal p53.

It was therefore necessary, at least initially, to abandon a replacement therapy which acted directly at the level of p53.

The present invention is therefore linked to studying the genes which are situated downstream of p53 in order to bypass the abovementioned difficulty.

In order to isolate the genes which are activated or inhibited by normal p53 (wild-type p53), a global screening was carried out of gene expression in a cell in which apoptosis had been induced and in the same malignant cell, more specifically in a cell which was expressing a p53 whose function was normal and in a cell which was expressing a p53 which was mutated and whose function was oncogenic. Comparison of the expressed genes (messenger RNAs expressed in the two types of cell) made it possible to identify genes which were expressed differentially, that is which were expressed in one of the cells but not the other (the genes can be activated or inhibited).

It was readily deduced that these genes are involved in the process of canceration, in the one case by their absence, and in the other case by their presence.

The method used for carrying out this differential study is the method described in 1992 by Liang and Pardee (Differential display of eucaryotic mRNA by means of a polymerase chain reaction) *Science* 257: 967–971 (1992), which is herewith incorporated by reference.

Until now, genes involved in suppression have been isolated either by positional cloning or by using double hybrids. The first method has made it possible, by making a statistical computation, to calculate the greatest probability of where a suppressor gene which was a candidate for a rather specific type of cancer, in particular those of familial origin, might be located within the chromosome. The double hybrid system enables the proteins which interact with a given gene to be isolated one by one.

The approach to the problem which was adopted in accordance with the present invention made it possible to isolate sequences which were directly linked to a function. As a result, in contrast to the random sequencing of the ESTs, the sequences are sequences whose function is known and which are involved in the apoptosis process which is induced by the p53 suppressor gene.

More precisely, this method was used on a cell model described by Moshe Oren; this model involves mouse myeloid tumor cells which have been transfected with a stable mutant of the p53 gene. Expression of this gene is temperature-sensitive, i.e. when the cells are cultured at 37° C., the protein which is produced is a mutated protein, that is to say it cannot act as a tumor suppressor and the corresponding cell line therefore develops in the form of malignant cells; by contrast, at a temperature of 32° C., the p53 protein which is expressed is able, like the natural protein, to act as a suppressor, and prevents the corresponding cell line from becoming malignant.

This systematic study made it possible to identify the genes which are involved in the suppression cascade which is induced by p53. More particularly, the inventors discovered that one gene, TSAP3, is responsible for apoptosis and/or tumor suppression.

For this reason, the present invention relates to these novel sequences and the genes which comprise them, as well as to the use of these sequences, both in diagnosis and therapy, and also for creating models for testing antineoplastic products.

The present invention relates, first of all, to a nucleotide sequence which corresponds to a gene which comprises:

(a) a sequence according to one of the SEQ ID Nos 1 to 10, or an equivalent gene which comprises:

(b) a sequence which hybridizes with one of the sequences according to (a), (c) a sequence which exhibits at least 80% homology with (a) or (b), or (d) a sequence which encodes a protein which is encoded by a gene according to (a), (b) or (c), or which encodes an equivalent protein, and their application, in particular in the suppression of cancer and in the therapeutic follow-up.

In addition, the present invention relates to a human gene which is involved in the suppression cascade induced by p53, and to the use of the sequences of this gene, both in diagnosis and in therapy, and also for creating models for testing antineoplastic products and their application as antiviral agents.

The present invention therefore also relates to a nucleotide sequence which corresponds to a gene which comprises:

(a) a sequence according to SEQ ID Nos 11, corresponding to the human TSAP 3 gene or HUMSIAH (Human Homologue of the Drosophila seven in absentia gene), or an equivalent gene which comprises:

(b) a sequence which hybridizes with one of the sequences according to (a), (c) a sequence which exhibits at least 80% homology with (a) or (b), or (d) a sequence which encodes a protein which is encoded by a gene according to (a), (b) or (c), or which encodes an equivalent protein, and their application, in particular in the suppression of cancer and in the therapeutic follow-up.

With regard to sequences 1 to 11, the present invention covers both the nucleotide sequence which corresponds to the entire gene and fragments of this gene, in particular when they encode an equivalent protein, as will be described below.

The nucleotide sequences can equally well be DNA sequences or RNA sequences or sequences in which some of the nucleotides are unnatural nucleotides, either in order to improve their pharmacological properties or to enable them to be identified.

The sequences mentioned in (b) (for SEQ ID Nos 1 to 11) are essentially sequences which are totally or partially complementary (in particular in the previously mentioned cases).

The (a) and (b) sequences (for SEQ ID Nos 1 to 10) provide access not only to the murine gene from which they are derived but also, by homology, to the corresponding human genes.

Thus, the invention also relates to the nucleotide sequences of the genes which exhibit strong homology with the previously mentioned genes, preferably a homology which is greater than 80% over the essential parts of the said genes, or, in general, at least 50% of the sequence; preferably, the homology over these parts is greater than 90%. "Homology" means the degree to which the sequences contain the same nucleotides when two nucleotide sequences are aligned and compared, using methods well known in the art of the invention.

Finally, when the said genes encode a protein, the present invention also relates to the sequences which encode the same protein, taking into account the degeneracy of the genetic code, and also equivalent proteins, that is to say which produce the same effects, in particular proteins which have been deleted and/or which have undergone point mutations.

The sequences according to the present invention are, more specifically, the sequences which are induced or inhibited at the time of cell apoptosis, in particular those which are induced by p53, or which are responsible for apoptosis, as in the case of TSAS 3.

The said genes are grouped together in the TSAP or "Tumor Suppressor Activated Pathway" and designated TSAP 1 to TSAP 8 and human TSAP 3, corresponding to SEQ ID Nos 1 to 8 and 11 (HUMSIAH) respectively, and the TSIP or "Tumor Suppressor inhibited Pathway" and designated TSIP 1 and TSIP 2, corresponding to SEQ ID Nos 9 and 10.

The characteristics of the sequences which correspond to SEQ ID Nos 1 to 10 are compiled in the appended table.

The nucleotide sequences which correspond to the TSAP genes (including human TSAP 3 or HUMSIAH) are sequences which are expressed during the apoptosis process, whereas the process of oncogenesis takes place when they are not expressed. It is therefore of interest:

to detect any anomaly in the corresponding gene which might lead to greater susceptibility to oncogenesis, and to be able to plan a replacement therapy.

It must also be recalled that these genes are able to intervene in other processes besides oncogenic processes; thus, p53 is, as it were, the guardian of the integrity of the genome; under these conditions, the TSAP or TSIP genes are doubtless also involved in this control function; the previously mentioned detection and therapy can therefore cover all the possible alterations of the genome. By contrast, the TSIP genes are expressed during oncogenesis and not during apoptosis; it is therefore also of interest in this case to detect any possible anomalies in the TSIP genes and to plan an inhibition/blocking therapy.

The replacement therapy can be effected by means of gene therapy, that is by introducing the TSAP gene together with the elements which enable it to be expressed in vivo. The principles of gene therapy are known. Specific viral or nonviral vectors can be used, for example adenovirus, retrovirus, herpesvirus or poxvirus vectors. Most of the time, these vectors are used in defective forms which serve as TSAP-expressing vehicles, with or without integration. The vectors can also be synthetic vectors, that is to say which mimic viral sequences, or else consist of naked DNA or RNA in accordance with the technique developed by the VICAL company, in particular.

In most cases, it is necessary to provide targeting elements which ensure expression which is specific for tissues or organs; thus, it is not possible to consider activating a phenomenon of uncontrolled apoptosis.

The present invention therefore relates to all the previously described vectors.

The present invention also relates to the cells which are transformed by an expression vector such as previously described as well as to the protein which can be obtained by culturing transformed cells.

The expression systems for producing proteins can be either eucaryotic systems, such as the preceding vectors, or procaryotic systems in bacterial cells.

One of the important features of the present invention is that it has demonstrated the involvement of several genes in apoptosis; thus, the use of gene therapy to over-express one of the genes may, for some of the genes, only lead to apoptosis of the cells in which other deregulated genes are already being expressed, that is malignant cells.

The present invention also relates to a compound, as a medicament, which ensures cellular expression of at least one of the previously mentioned nucleotide sequences, in particular of the TSAP 1 to TSAP 8 and human TSAP 3 genes, when it is induced during cell apoptosis, or, on the contrary, which ensures inhibition of the cellular expression of at least one cell sequence such as previously described, in particular TSIP 1 and TSIP 2, when it is inhibited during cell apoptosis.

It is, for example, possible to envisage approaches other than gene therapy, in particular the use of nucleotide sequences in a sense or antisense strategy, that is to say sequences which are able to block TSIP expression or which, on the contrary, acting upstream, promote TSAP expression.

It is also possible to envisage a direct replacement strategy which involves supplying proteins which correspond to TSAP or inhibitory antibodies which correspond to TSIP.

Finally, it is possible to envisage using non-protein molecules whose activity is to activate TSAP or to mimic the action of its expression product or else to inhibit TSIP or else to block the action of its expression product.

These products can be easily tested on modified cells, which are described in the examples, by introducing the products to be tested into the cell culture and detecting the appearance of the apoptotic phenomenon. In the strategies using DNA, RNA or protein, the products are, of course, developed in accordance with the sequences which are described.

The present invention relates, in particular, to the use of the abovementioned medicaments as antineoplastic agents.

However, the product of the human TSAP 3 gene (HUMSIAH) may also be used as an antiviral agent, as will be apparent from reading Example 2. The present invention therefore also relates to the use of the abovementioned medicaments as antiviral agents.

The present invention also relates to all or part of the sequences according to the invention for use, in the role of a diagnostic agent for determining predisposition to cancer, as a nucleotide probe or as an amplification primer, and, also in the role of diagnostic agent for determining predisposition to cancer, to an antigen which corresponds to all or part of the proteins encoded by the sequence according to the invention or to the corresponding antibodies, in particular monoclonal antibodies, where appropriate following culture.

The diagnostic methods are known; they can, for example, be techniques for microsequencing variable parts following isolation and possible amplification, or detection methods of the RFLP type, or straightforward amplification in particular. The differential techniques can, in particular, make it possible to demonstrate the divergence between normal and abnormal TSAP or TSIP.

The invention also relates to models which make use of the abovementioned sequences. The PCR method, or other amplification methods, may be employed, in particular, to isolate the human TSAP 3 gene (HUMSIAH) by utilizing the structure of the gene. It is also possible to synthesize this gene bit by bit, if required.

Finally, the invention relates to an improvement to the method of Liang and Pardee, Science 257: 967–971 (1992), which involves carrying out a stepwise decrease ("touch down"), as described in Don et al. Nucl. Acids Res. 19: 4008 (1991), in the PCR amplification. Liang et al and Don Et al are herewith incorporated by reference.

DESCRIPTION OF THE FIGURES

C1: mRNA also expressed using a clone without differential expression;
C2: positive control using Cyclin G and showing induction of the mRNAs corresponding to 32° C.;
MER-LTR: showing induction of this sequence at 32° C.;
TSAP 1 to TSAP 8: differential expression of the 8 activated mRNAs in the first 4 hours following the induction of apoptosis;
TSIP 1 and TSIP 2: differential expression of the 2 mRNAs which are inhibited in the first 4 hours following the induction of apoptosis.

FIG. 4—Comparison of the TSAP 1 cDNA sequence (SEQ ID NO: 1) and the nucleotide sequence corresponding to rat beta 4 phospholipase C (SEQ ID NO: 13).

FIG. 5—Comparison of the TSAP 2 cDNA sequence (SEQ ID NO: 2) and the nucleotide sequence corresponding to the zinc finger protein (ZFM 1) (SEQ ID NO: 14) which is located in the multiple endocrine neoplasia (MEN 1) locus.

FIG. 6—Comparison of the TSAP 3 cDNA sequence and the nucleotide sequence corresponding to the murine homolgoue, MMSIAH 1B gene.

FIG. 7—Comparison of the product of the sina genes of different species, human (SEQ ID NO: 17)(HUMSIAH), murine (SEQ ID NO: 18 & 19 respectively ) (MMSIAH 1B) 1A and Drosophila (SEQ ID NO: 20) (DROSINA).

FIG. 8—Comparison of the TSIP 2 cDNA sequence (SEQ ID NO: 10) and the cDNA sequence of the murine S182 transcript (SEQ ID NO: 16) of the AD3 gene, which is involved in Alzheimer's disease.

FIG. 9A shows the results of a FACS analysis of the DNA content in U937 cells transfected with the vector alone (RSV-C) and those transfected with TSAP 3 (RSV-7S. Respectively, 3% and 12% of the cell population is in the sub G1 phase. FIG. 9B shows the results of a FACS analysis of the TUNEL assay with 3% of the U937 cells transfected with the vector along (RSV-C), as compared to 15% of the U937 cells transfected with TSAP 3 (RSV-7S) being positive.

FIG. 9C shows the results of a tumorigenicity assay in SCID/SCID mice. After injection with either U937 cells transfected with the control vector alone (—O— RSV C), mice form large tumors in 20 out of the 20 injection sites and appear early. The U937 cells stably transfected with TSAP 3 (-φ- RSV-75) form smaller tumors. * indicates the statistical significance: $p \leq 0.001$.

FIG. 10A shows expression of TSAP 3 during wt-p53 induction of apoptosis. Specifically this is the results of a Western blot analysis with anti-TSAP3 antibodies generated against the first 16 amino acids of TSAP. Lane 1- LTR-6 cells at 37° C. Lane 2- LTR6 cells after 4 hours of incubation at 32° Lane 3- LTR-6 cells after 7 hours of incubation at 32° C. Lane 4- LTR-6 cells after 9 hours of incubation at 32° C. Lane 5- LTR-6 cells after 16 hours of incubation at 32° C. Lane 6- LTR-6 cells after 24 hours of incubation at 32° Arrow indicates the 30 kDa TSAP 3 protein. FIG. 10B shows the subcellular localization of TSAP 3, via Western blot with anti-TSAP 3 antibodies. Lane 1- nuclear fraction of LTR-6 cells after 4 hours of incubation at 32° C. Lane 2-membrane fraction of LTR-6 cells after 4 hours of incubation at 32° C. Lane 3-cytoplasmic fraction of LTR-6 cells after 4 hours of incubation at 32° C. Arrow indicates the 30 kDa TSAP 3 protein. FIG. 10C shows expression of TSAP 3 in U937 cells with a suppressed malignant phenotype. Lane 1- U937 cells transfected with the control vector alone. Lane 2- US cells derived from U937 cells but displaying a suppressed malignant phenotype. Lane 3- U937 cells stably transfected with TSAP 3 (clone RSV-7S). Lane 4- U937 cells stably transfected with TSAP 3 (clone RSV-8S). Lane 5- U937 cells stably transfected with TSAP 3 (clone RSV-10S).

EXAMPLES

Figure 1:
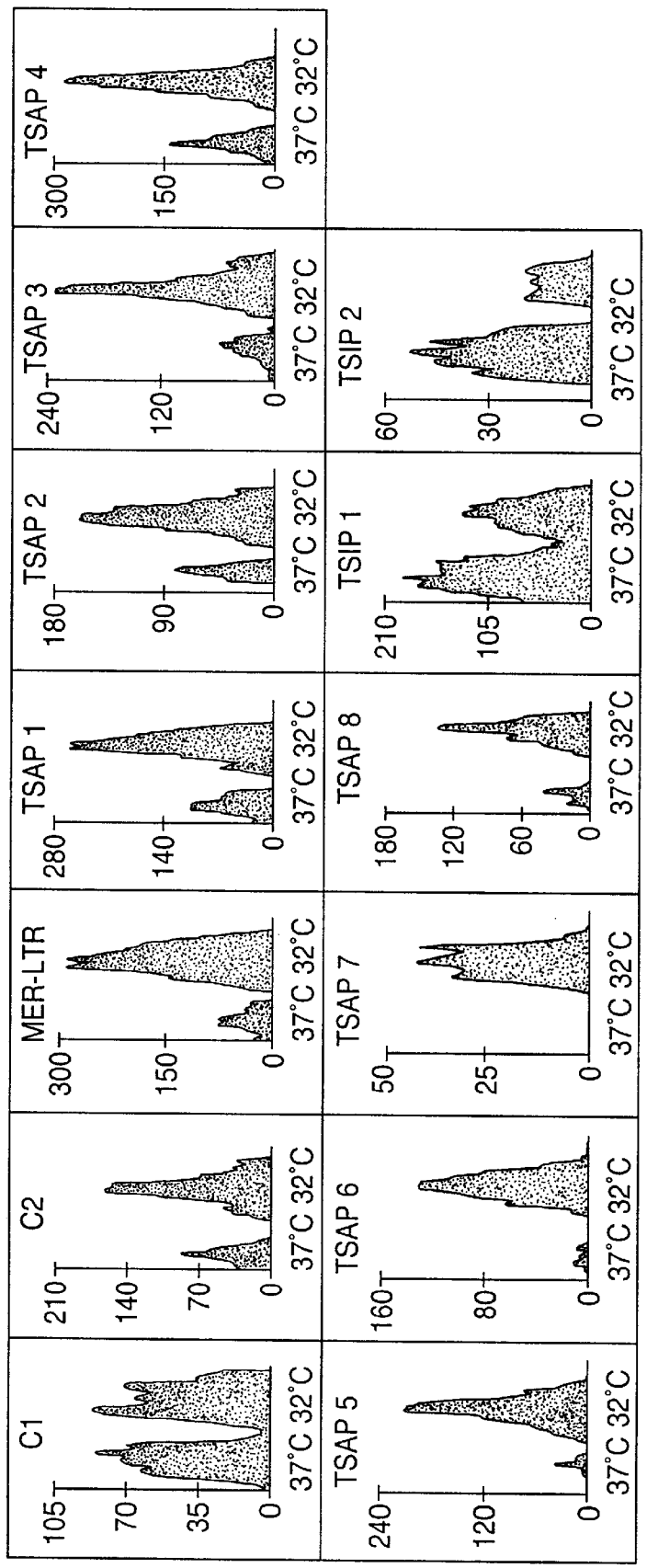
FIG. 1—Quantification of the differential expression of the mRNAs using a 1200 β imager. Hybridization to mRNAs derived from LTR6 cells at 37° C. and LTR6 cells after 4 hours at 32° C. The numbers on the ordinates from 0 to 500 correspond to counts detected per 0.15 mm and are proportional to the hybridization signal.

The following general methods were used in the examples which follow and which are not intended to limit the invention in anyway.

MATERIALS AND METHODS

Cell Cultures

M1 myeloid leukemia cells (clone S6) and M1 cells which are stably transfected with a temperature-sensitive mutant, val 135 p53 (LTR6) (3), Yonish-Rouach et al., *Nature* 352: 345–347 (1991).

These cells are cultured on RPMI 1640 medium containing 10% FCS at 5% $CO_2$ and 37° C. In order to change the temperature, the cultures are placed in a second incubator at 32° C. In all the assays carried out in this study, the cells are tested for the presence of apoptosis after 12 and after 24 hours.

Study of the Differential cDNAs

The following modifications of the original protocol by Liang et at. (1) were made in order to carry out the tests under standard experimental conditions and obtain total reproducibility of the results.

Use is always made of polyA+ mRNAs which have been purified twice on an oligodT column making use of Fast Track (Invitrogen, San Diego Calif.). After reverse transcription (M-MLV Reverse Transcriptase, Gibco BRL) on 0.05 μg of polyA+ using 20 μm of each of the dNTPs (Boehringer-Mannheim), no additional dNTP is added to the final PCR mixture. A "hot start" at 94° C. is carried out for 5 minutes before the PCR (GeneAmp PCR system 9600, Perkin Elmer Cetus). The samples are cooled down rapidly in ice water. A "touch down" (Don et at., supra)(2) of 10 cycles or 50° C. to 40° C. is carried out (94° C. 30 seconds –50° C. 1 minute –72° C. 30 seconds), followed by 35 cycles (94° C. 30 seconds –40° C. 1 minute –72° C. 30 seconds) and a final extension of 5 minutes at 72° C. The PCR products are separated on non-denaturing 6% polyacrylamide gels (Bauer et al., Nucl. Acids Res. 21: 4272–4280 (1993)(4). The gels are exposed without drying. Each differential presentation is performed by comparing M1S6 and LTR6 at 37° C., and after incubating the two cell lines at 32° C. for 4 hours.

The differential presentation procedure is repeated in 3 different experiments in order to confirm complete reproducibility.

The bands which are expressed differentially are excised from the gel, eluted and reamplified (1). The PCR products are subcloned using the TA-cloning system (Invitrogen, San Diego, Calif.) in accordance with the instructions supplied.

For each ligation reaction, 10 recombinant clones are sequenced using the automated ABI system.

Extraction of the RNAs, and Northern Blot Probes and Analyses

The total RNA is extracted using Trizol (Life Technologies). The polyA+ RNAs are prepared using an OligotexdT kit (Qiagen, Calif.). 30 μg of total RNA or 2 μg of polyA+ RNA are separated on a 1% agarose/1×MOPS/2% formaldehyde gel, transferred onto a nylon membrane (Hybond N+, Appligene, France) as has been previously described (Sambrook et at., *Molecular Clotting: a laboratory manual* (1989) (5). The Northern blots are hybridized with $P^{32}$-labeled probes on the TSAP and TSIP inserts and washed as previously described (Sambrook et at, supra). In order to check that the function of the wild-type p53 has been induced, the Northern blots are hybridized with a cyclin G probe (Okamoto, et al., *EMBO J.*, 13: 4816–4822 (1994). As a control for the quantity of mRNA which has been loaded on, the blots are hybridized with a GAPDH probe. Different Northern blots (Clontech, Calif.) are used under identical conditions and hybridized, as a control, with a β-actin probe. The RT-PCR products in the case LTR6 are amplified using the following siah 1b primers (SEQ ID NOS 21 & 22, respectively): 5'CAGTAAACCACTGAAAAACC3' and 5'CAAACCAAACCAAAACCAC3'. The subcloned PCR product is used as a control siah 1b probe. The Northern blots are exposed at –80° C. for 10 days.

Slot Blots

The reproducibility of the results obtained by the Northern blot analyses. The blots are prepared (bio-Rad, Hercules, Calif.) by placing the PCR products (200 ng of Zeta-Probe Blotting Membranes, Bio-Rad, in accordance with the manufacturer's instructions) of TSAP clones and hybridized with a $P^{32}$-labeled cDNA probe (Superscript II Gibco-BRL, Life Technologies) corresponding to the RNA of LTR6 cells which have been incubated at 37° C. and then at 32° C. for 4 hours. The PCR product of the clone containing cyclin G is also deposited on the membranes and used as a positive control. The slot blots are exposed at –80° C. overnight.

Quantitative Image Analysis

This is performed on the two Northern blots (for TSIP 1 and TSIP 2), and on the slot blots for all the control cDNAs and TSAP 1 to 8, using a 1200 β imager (Biospace instruments, Paris, France). For the quantitative analysis represented in the graphs in FIG. 1, a constant number was subtracted from each peak. This constant is calculated by measuring the mean value of the background noise in the slots which do not contain any cDNA. The β imager results were obtained by counting the slot blots overnight and by confirming them by means of autoradiography using variable exposure times. These autoradiograms show the same relative qualitative variations between the activities at 32° C. and 37° C. as do the measurements obtained using the β imager.

In-situ Hybridization (7, 8)

The cells are washed 3 times in a saline phosphate buffer (PBS), "cytospinned" and fixed with 4% paraformaldehyde in PBS for 10 minutes, and then stored in 70% ethanol. RNA transcripts of TSAP 3 which are labeled with digoxigenin-11-uridine-5'-triphosphate (DIG) and biotin-11-UTP are used in the analyses in accordance with the previously described procedure (Boehringer-Mannheim). In order to detect strains labeled with hybridized digoxigenin, the slices are incubated in SAD-10 (10 nm of gold-labeled sheep anti-DIG antibody diluted 1/1000, Biocell UK). The analysis is performed using confocal laser microscopy. See Atigerer et al., *Methods in cell biology: functional organization of the nucleus*, 35: 37–71 (1991) and Linares-Cruz et al., *J. Microsc.* 173: 27–38 (1994).

Example 1

Differential study of the cDNAs using the Liang and Pardee method provides a very powerful and efficient tool for detecting variations in gene expression. Nevertheless, it was necessary to modify the original protocol, as has previously been pointed out, in order to eliminate some problems of reproducibility which were observed when applying the method as originally described.

Complete reproducibility was found when a "hot start" followed by a "touch down" were introduced into the PCR method.

Nevertheless, after having been isolated and reamplified, the differentially expressed bands are often contaminated with bands arising from the RNAs which migrate into the regions adjacent to the cDNA; errors result if these probes are used directly on Northern blots. The second PCR products were therefore subcloned and Northern blot analyses, used for lack of a single probe recombinant, were carried out. The systematic sequencing of at least 10 recombinant subclones in the case of each selected band showed that this was very effective for selecting the clones of interest.

In die current state of knowledge, the p53 gene is the tumor suppressor which is mutated in the largest number of cancers of very diverse origin, and use of the temperature-sensitive mutant val-135 p53 has already previously been shown to provide a very considerable amount of information regarding the function of the wild-type p53 in inducing either cessation of cell growth in the G-1 phase or initiation of the program of cell death.

Until now, the molecular pathways upstream and downstream of p53 which lead to tumor suppression have been very unclear.

A certain number of genes downstream of p53 have previously been identified; these are, in particular, gadd 45, mdm 2, mck, mouse endogenous retrovirus LTR, p21-waf and cyclin G.

The present invention has demonstrated the existence of 11 genes which are expressed differentially in cells which are expressing p53 in its active suppressor form or else in tumor cells which are expressing the inactive p53 gene.

FIG. 1 shows a quantification of the hybridization signals which correspond to the differential expression of 8 of these genes which are activated at 32° C., that is to say in which the wild-type p53 function is activated and therefore leads to apoptosis of the cells; in that which follows, these activated genes will be designated TSAP (for tumor suppressor activated pathway); by contrast, it is observed that, in two experiments, 2 genes which are expressed at 37° C. are partially inhibited at 32° C., implying that they are inhibited during programmed cell death; these genes were designated TSIP (for tumor suppressor inhibited pathway).

Analysis of the homologies of the different activated sequences of TSAP 1 to TSAP 3 showed that these genes were already known. By contrast, the other cDNAs, i.e. the TSAP 4 to TSAP 8 cDNAs, do not show any significant homology with known genes.

The cDNA corresponding to TSIP 1, whose expression is inhibited during apoptosis, does not exhibit any homology with known genes.

The cDNA corresponding to TSIP 2, whose expression is also inhibited during apoptosis, shows a high degree of homology with the S182 transcript of the AD3 gene, which is involved in the metabolic pathways of Alzheimer's disease (Sherrington et al., *Nature* 375: 754–760 (1995)) (FIG. 8).

Consequently, it is possible to act on the metabolic pathways of Alzheimer's disease by acting on the p53-dependant metabolic pathways.

The present invention therefore also relates to a compound, as a medicament, which ensures the cellular expression of TSIP 2 and which is intended for treating Alzheimer's disease, and to all or part of the TSIP 2 sequence for use, in the role of a diagnostic agent for determining predisposition to Alzheimer's disease, as a nucleotide probe or as an amplification primer, and also to an antigen which corresponds to all or part of the proteins encoded by TSIP 2, or to the antibodies, in particular the corresponding monoclonal antibodies, where appropriate after culture.

The hypothesis which can be put forward with regard to the genes whose expression is inhibited by wild-type p53 is that they may encode oncogenic sequences which are regulated downstream of the process of tumor suppression or else that it is a matter of structural or cytoskeletal proteins, the regulation of which downstream of expression occurs concomitantly with cell death by apoptosis.

TSAP 1 is homologous with rat beta 4 phospholipase C. The TSAP 1 sequence exhibits 100% identity with PLC between nucleotides 3967 and 3985; 82% identity between nucleotides 3986 and 4116 and 85% identity between nucleotides 4070 and 4220 (FIG. 4). PLC is known to be involved in the tyrosine kinase receptor signalling pathway and to catalyze the hydrolysis of phosphatidylinositol-4,5-biphosphate to diacylglycerol and inositol-1,4,5-triphosphate. However, the present studies suggest that PLC is a downstream target in p53-mediated apoptosis.

TSAP 2 exhibits sequences which are conserved (92% identity between nucleotides 259 and 299; 100% identity between nucleotides 418 and 458 and 92% identity between nucleotides 645 and 685) between it and the zinc finger protein (ZFM 1), which is located in the multiple endocrine neoplasia (MEN 1) locus (FIG. 5). MEN 1 is an autosomal dominant disorder which is associated with the development of tumors which affect the anterior lobe of the pituitary and parathyroid glands and the cells of the pancreatic ilots. It is particularly interesting to have demonstrated that both ZFM and an isoenzyme of PLC are co-located in the same chromosomal region, i.e. 11q13, which contains the gene for susceptibility to MEN 1. In mice, the homologous regions are located on chromosome 19B. The fact that TSAP 1 and TSAP 2 are found to be activated in response to p53 may suggest that these genes belong to a more global tumor suppression pathway and that p53 is able to cooperate with MEN 1.

Figure 2:
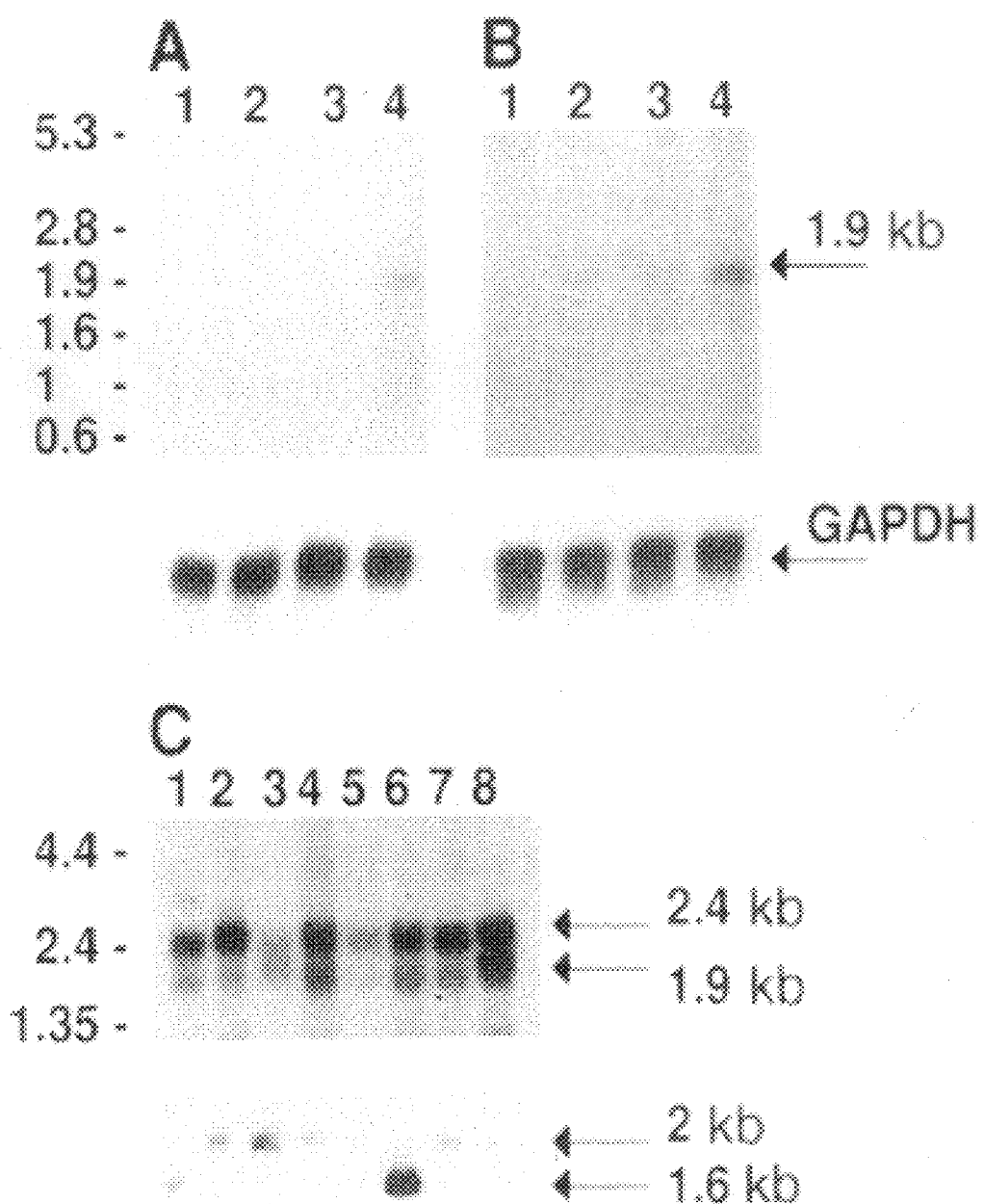
FIGS. 2A–2C: Northern blot analysis.
A: hybridization with the TSAP 3 probe;
B: hybridization with the mouse siah 1b probe;
tracks 1 and 2: polyA+ mRNA of M1 myeloid leukemic cells (clone S6) cultured at 37° C. and 32° C., respectively;
tracks 3 and 4: polyA+ mRNA of LTR6 cells cultured at 37° C. and 32° C., respectively;
the arrow indicates the differential expression of the TSAP 3 1.9 kb transcript—mouse siah 1b;
lower panels: GAPDH;
C: tissue distribution using TSAP 3 as a probe;
1: heart, 2: brain, 3: spleen, 4: lung, 5: liver, 6: skeletal muscle, 7: kidney, 8: testicle;
the arrows indicate the 1.9 and 2.4 kb transcripts; lower panel: β-actin.
Figure 3:
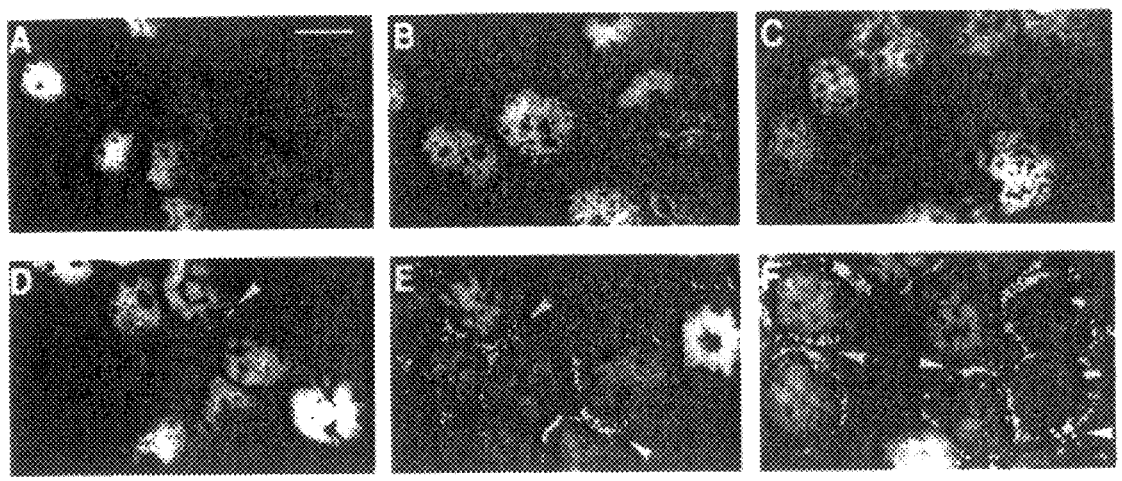
FIG. 3—Analysis of in-situ hybridization using the TSAP 3 probe;
A: M1 cells incubated at 32° C. for 4 hours and hybridized with an antisense TSAP 3 probe;
B: LTR6 cells incubated at 32° C. for 4 hours and hybridized with a sense TSAP 3 probe;
C: LTR6 cells incubated at 37° C. and hybridized with an antisense TSAP 3 probe;
D to F: LTR6 cells cultured at 32° C. for 1, 2 and 4 hours, respectively, and hybridized to an antisense TSAP 3 probe;
the bar in panel A: 10 μm;
the arrows indicate accumulation of the TSAP 3 mRNAs in the cytoplasm.

TSAP 3 is identical to Siah 1b. This gene is the vertebrate homologue of the Drosophila seven in absentia (sina) gene. The described clone exhibits 94% identity with the murine homologue (nucleotides 1496 to 1634) (FIG. 6). Differential expression of a 1.9 kb messenger from this gene has been detected by means of Northern blot analysis using a TSAP 3 probe (FIG. 2A). This is confirmed by using a second probe which corresponds to the same region of the described siah 1b sequence (FIG. 2B). FIG. 2C shows the tissue distribution of this gene, using a TSAP 3 probe which detects, at one and the same time, mRNAs of 1.9 and 2.4 kb in size, corresponding to the previously mentioned results when a siah probe is used. The in-situ hybridization shows that the TSAP 3 mRNA is rapidly induced 1 hour after inducing apoptosis (FIG. 3D). Its expression increases after 2 and 4 hours (FIGS. 3E and 3F). No signal is detected in the cells which have entered mitosis.

Carthew and Rubin have shown that seven in absentia is required for eye development in drosophila. On the other hand, mutants of this gene exhibit a much more general role in development in drosophila. The murine homologue is subdivided into two groups, i.e. siah 1 and siah 2, and these proteins exhibit a degree of conservation in relation to drosophila seven in absentia which is altogether unusual.

Results have shown that TSAP 3/siah 1b is activated in the cell death program in M1 cells which are induced by the p53 tumor suppressor gene. Since this gene encodes a nuclear zinc finger protein, it could be a regulatory transcription factor which is downstream of the p53 signal. The results also show a direct link between the genes which are concerned with development in drosophila and a major tumor suppression pathway.

Example 2

The above-described murine cDNA fragment (TSAP 3), which was obtained by differential analysis of mRNA, was used to make a probe for isolating a 1.1 kb fragment from a human cDNA library, which fragment was then expanded to encompass the entire coding region by means of RACE-PCR.

FIG. 7 shows the cDNA and the amino acid sequence of the human sina gene (TSAP 3).

This sequence encodes a 282 amino acid protein which has a C3HC4 zinc finger motif. This protein also exhibits analogies with proteins which are able to attach to RNA. The amino acid sequence is very highly conserved between the drosophila, mouse and human genes (FIG. 7). The tissue distribution indicates that human sina is expressed ubiquitously and encodes an mRNA of 2.3 kb; in the placenta, there is an additional transcript of 2.5 kb in size.

It was possible to isolate 8 YACs (350–1000 kb) and 2 BACs (100 and 125 kb) by analyzing the YACs of the CEPH and BAC libraries by means of PCR using specific human sina primers.

Using the YAC and BAC clones, fluorescence by in-situ hybridization (FISH) shows that the seven in absentia is located on chromosome 16q12–13, that is in a region which contains the genes which are candidate tumor suppressor genes in various cancers, in particular: breast cancer (Bieche, et al., *Genes Chromosomes and Cancer* 14: 227–251 (1995)), Wilm's tumor (Wang-Wuu, et at. *Cancer Res.* 50: 2786–2793 (1990), Maw, et al. *Cancer Res.* 52: 3094–3098 (1992), Austruy et al., *Genes, Chromosomes and Cancer* 14: 285–294 (1995)), Laurence, Moon, Bard and Biedl's syndrome (Kuytek-Black et al. *Nat. Genet.* 5(4): 392–396 (1993)) and Beckwith and Wiederman's syndrome (Newsham et al. *Genes, Chromosomes and Cancer* 12(1): 1–7 (1995)).

As was pointed out in French patent application No. 95 15 146, it was found that murine M1 cells which were stably transfected with mutant temperature-sensitive p53 exhibited activation of seven in absentia following induction of apoptosis at 32° C. Given the fact that the murine TSAP 3 was isolated in an apoptosis model induced with the p53 gene, it was logical to extend the analysis of the TSAP 3 (HUMSIAH) gene in a model of human physiological apoptosis.

This model is described in the intestine, where the cells migrate from the bottom of the crypt toward the apical region of the villosities, where they die by apoptosis before being released into the lumen. These apoptotic cells are specifically labeled by means of the TUNEL technique. Moreover, in physiological apoptosis in man, these same cells are positive for the TSAP 3 (HUMSIAH) gene by in-situ hybridization.

Finally, in order to investigate the involvement of the human TSAP 3 gene in tumor suppression, use was made of a model which is based on all the genes rather than on a single gene. This model is based on the biological properties of the H-1 parvovirus.

Very exhaustive research in this area has demonstrated over the last 20 years that parvovirus preferentially kills tumor cells while sparing their normal counterpart.

So as to construct a model, the following hypothesis was put forward: if it were possible to select cells which were resistant to the cytopathic effect of H-1 parvovirus from a tumor which is sensitive to this effect, this resistance might be due to a change in the malignant phenotype of these resistant cells. It was possible to demonstrate this in the case of KS cells which were selected from human K562 erythroleukemic cells. While the parental K562 cells are sensitive to the cytopathic effect of the H-1 parvovirus, the KS cells are resistant. These resistant cells re-express the wild-type p53 and have a phenotype which is suppressed both in vitro and in vivo.

In order to confirm these observations on other cells, daughter US3 and US4 cells were selected from a monoclone of a human U937 monocytic leukemia. These clones are resistant to the cytopathic effect of H-1 parvoviruses and exhibit in vivo reversion of the malignant phenotype. Analysis of the surface markers on 20 cells indicates that there is no shift between U937 and the US clones in the stage of differentiation, in turn indicating that suppression of the malignant phenotype is not due to terminal differentiation.

Neither the K562 nor the U937 cells express p53. In contrast to the KS cells, which re-express p53, the US3 and US4 cells do not re-express p53. Nevertheless, it was possible to show that the US3 and US4 cells exhibited activation of WAF-1 as compared with the malignant parental U937 cells. Such activation of WAF-1, in an alternative, p53-independent pathway, has recently been described, and the current results show that the US3 and US4 clones appear to use this alternative WAF-1 pathway.

The sina gene is activated by the wild-type p53 which can be induced in M1 cells as well as in the KS cells which re-express the wild-type p53.

While the parental U937 cells only express sina mRNA to a very low degree, expression of this mRNA is activated in the daughter US3 and US4 clones, whose malignant phenotype has reverted and which are re-expressing $p21^{waf-1}$.

Interestingly, sina is activated in cells which become apoptotic, as has been demonstrated by means of double labeling using a sina probe for in-situ hybridization combined with a TUNEL assay.

This demonstrates that the human sina gene, which is very conserved in phylogeny, is involved in apoptosis and tumor suppression.

Still more importantly, sina is located at the intersection of the p53 and WAF-1 pathways.

In addition, it was possible, using the U937, US3 and US4 model, to demonstrate that the suppressor molecules are functionally linked by using a global biological model which compares parental malignant cells and directly derived daughter cells at molecular levels. These experiments indicate that it is not necessary to transfer specific human tumor suppressor genes so as to confer on them the suppressor phenotype and that, on the contrary, tumor reversion is under the control of a regulatory system which is always present in the genetic material of the tumor cells even if it is necessary to reactivate it.

Figure 9:
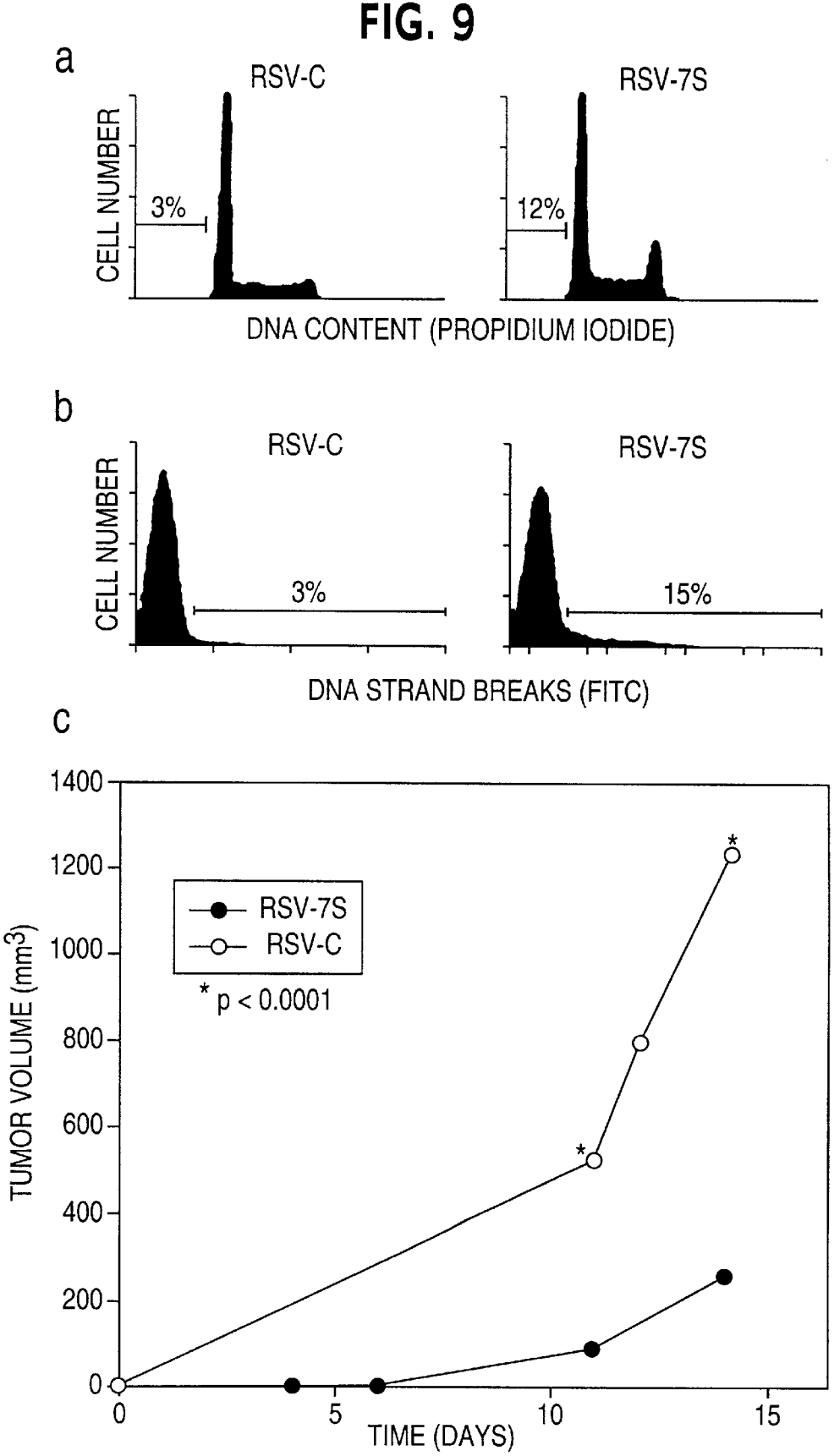
FIGS. 9A–9C—Shows the biological effects of TSAP 3 expression in U937 cells.
Figure 10:
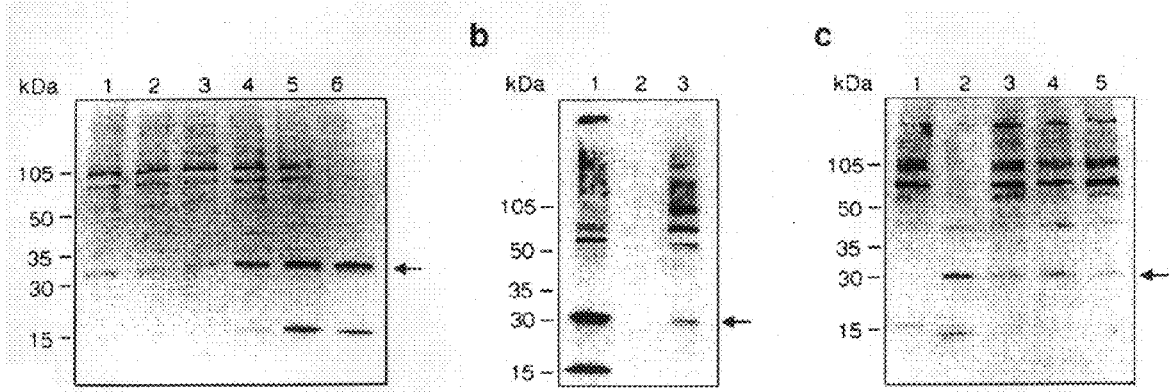
FIGS. 10A–10C—This figure shows the characterization of the TSAP 3 protein.

The results depicted in FIG. 9 establish the direct effect of TSAS 3 on apoptosis. FIG. 9A shows the results of a FACS analysis of the DNA content in U937 cells transfected with the vector alone (RSV-C) and those transfected with TSAP 3 (RSV-7S). Respectively, 3% and 12% of the cell population is in the sub G1 phase. FIG. 9B shows the results of a FACS analysis of the TUNEL assay with 3% of the U937 cells transfected with the vector alone (RSV-C), as compared to 15% of the U937 cells transfected with TSAP 3 (RSV-7S) being positive. FIG. 9C shows the results of a tumorigenicity assay in SCID/SCID mice. After injection with either U937 cells transfected with the control vector alone (—O— RSV C), mice form large tumors in 20 out of the 20 injection sites and appear early. The U937 cells stably transfected with TSAP 3 (-•- RSV-75) form smaller tumors. (* indicates the statistical significance: $p \leq 0.001$) This tumorigeneicity test shows the TSAP 3 gene's suppression of tumorigenicity in vivo FIG. 10 shows the characterization of the TSAP 3 protein. FIG. 10A shows expression of TSAP 3 during wt-p53 induction of apoptosis. Specifically this is the results of a Western blot analysis with anti-TSAP3 antibodies generated against the first 16 amino acids of TSAP 3. Lane 1- LTR-6 cells at 37° C. Lane 2- LTR-6 cells after 4 hours of incubation at 32° Lane 3- LTR-6 cells after 7 hours of incubation at 32° C. Lane 4- LTR-6 cells after 9 hours of incubation at 32° C. Lane 5- LTR-6 cells after 16 hours of incubation at 32° C. Lane 6- LTR-6 cells after 24 hours of incubation at 32° Arrow indicates the 30 kDa TSAP 3 protein. FIG. 10B shows the subcellular localization of TSAP 3, via Western blot with anti-TSAP 3 antibodies. Lane 1-nuclear fraction of LTR-6 cells after 4 hours of incubation at 32° C. Lane 2-membrane fraction of LTR-6 cells after 4 hours of incubation at 32° C. Lane 3-cytoplasmic fraction of LTR-6 cells after 4 hours of incubation at 32° C. Arrow indicates the 30 kDa TSAP 3 protein. FIG. 10C shows expression of TSAP 3 in U937 cells with a suppressed malignant phenotype. Lane 1- U937 cells transfected with the control vector alone. Lane 2- US cells derived from U937 cells but displaying a suppressed malignant phenotype. Lane 3- U937 cells stably transfected with TSAP 3 (clone RSV-7S). Lane 4- U937 cells stably transfected with tSAP 3 (clone RSV-8S). Lane 5- U937 cells stably transfected with TSAP 3 (clone RSV-10S). In sum, it was possible to identify in the MI/LTR6 model, a 30 kDA TSAP 3 protein hat induces apopotosis.

TABLE

CHARACTERISTICS OF THE CLONES

| Differentially expressed clone | 3' and 5' primers* | Size of the mRNA in kb | Homology |
|---|---|---|---|
| TSAP 1 | T11GC-16 | 2.0 and 4.5 | PLC # |
| TSAP 2 | T11GC-5 | 5.9 | MEN1 § |
| TSAP 3 (IDS No.3) | T11CG-4 | 1.9 | siah 1b ¶ |
| TSAP 4 | T11GC-6 | 5.0 | No |
| TSAP 5 | T11CG-5 | 1.2 | No |
| TSAP 6 | T11AG-1 | 2.8 | NO |
| TSAP 7 | T11GC-16 | >8.0 | No |
| TSAP 8 | T11GC-6 | >10.0 | No |
| TSIP 1 | T11CG-8 | 3.0 | No |
| TSIP 2 | T11AA-5 | 3.1 | AD3✪ |

*the figures and the sequences of the 5' primers correspond to those reported by Bauer et al. ,supra (4)
rat beta 4 phospholipase C mRNA (RATPHOSCB)
§ human mRNAs (HUMMEN1C: HUMZFM1C: HUMZFM1A: HUMMEN1A)
¶ siah-1B mRNA (MMSIAH1B)
✪ AD3, murine S182 mRNA transcript (human S182 mRNA homologue) (Sherrington et al., supra).

Applicants hereby incorporate by reference all journal articles, patents and patent applications referred to above.

(1) Liang P. & Pardee A. B. (1992) Science 257, 967–971.
(2) Don R. H., Cox P. T., Wainwright B. J., Baker K. & Mattick J. S. (1991) Nucl. Acids Res., 19, 4008.
(3) Yonish-Rouach E., Resnitzky D., Lotem J., Sachs L., Kimchi A. & Oren M. (1991) Nature 352, 345–347.
(4) Bauer D., Muller H., Reich J., Riedel H., Ahrenkiel V., Warthoe P. & Strauss M. (1993) Nucl. Acids Res. 21, 4272–4280.
(5) Sambrook J., Fritsch E. F. & Maniatis T. (1989) Molecular Cloning: a laboratory manual.
(6) Okamoto K. & Beach D. (1994) EMBO J., 13, 4816–4822.
(7) Angerer L. & Angerer R. C. (1991) Methods in cell biology: functional organization of the nucleus, 35, 37–71.
(8) Linares-Cruz G., Rigaut J. P., Vassy J., De Oliveira T. C., De Cremoux P., Olofsson B. & Calvo F. (1994) J. Microsc., 173, 27–38.
(9) Bieche I. and Lidereau R., Genes Chromosomes and Cancer 14, 227–251 (1995).
(10) Wang-Wuu S., Soukup S., Bove K., Gotwals B. and Lampkin B., Cancer Research 50, 2786–2793 (1990).
(11) Maw M. A. et al., Cancer Research 52, 3094–3098 (1992).
(12) Austruy E. et al., Genes, Chromosomes and Cancer, 14, 285–294 (1995).
(13) Kuytek-Black A. E. et al., Nat. Genet 5(4)n 392–396 (1993).
(14) Newsham I. et al., Genes Chromosomes and Cancer 12(1), 1–7, (1995).
(15) Sherrington et al., Nature, vol. 375, p. 754–760 (1995)

We claim:

1. An isolated DNA molecule encoding TSIP 2, said isolated DNA molecule consisting of the nucleotide sequence of SEQ ID NO:10, wherein tumor suppression inhibits the expression of said TSIP gene.

2. The isolated DNA molecule of claim 1, wherein cell apoptosis inhibits expression of said TSIP 2.

3. A vector comprising said isolated DNA molecule of claim 1.

4. The vector of claim 3, which is a viral vector.

5. The vector of claim 4, wherein said virus is selected from the group consisting of an adenovirus, retrovirus, herpesvirus and poxvirus.

6. The vector of claim 3, wherein said vector is a naked plasmid.

7. The vector of claim 3, which further comprises a nucleic acid sequence that provides for expression of said DNA in a specific tissue.

8. An isolated host cell stably transformed with the vector of claim 3.

9. The isolated DNA molecule of claim 1, wherein cellular expression of said molecule is inhibited during cell apoptosis and wherein cell apoptosis is induced by p53.

* * * * *